US009183498B2

(12) United States Patent
Landers

(10) Patent No.: US 9,183,498 B2
(45) Date of Patent: Nov. 10, 2015

(54) HEALTH AND FITNESS MANAGEMENT SYSTEM

(71) Applicant: KINETIC STONE LLC, Edgweater, NJ (US)

(72) Inventor: David B. Landers, Edgewater, NJ (US)

(73) Assignee: KINETIC STONE, LLC, Edgewater, NJ (US)

( * ) Notice: Subject to any disclaimer, the term of this patent is extended or adjusted under 35 U.S.C. 154(b) by 161 days.

(21) Appl. No.: 13/743,718

(22) Filed: Jan. 17, 2013

(65) Prior Publication Data

US 2013/0132319 A1 May 23, 2013

(51) Int. Cl.
*G06N 99/00* (2010.01)
*G06N 5/02* (2006.01)
*G06F 19/00* (2011.01)

(52) U.S. Cl.
CPC .............. *G06N 5/02* (2013.01); *G06F 19/3475* (2013.01); *G06F 19/3481* (2013.01); *G06F 19/3406* (2013.01); *G06F 19/3487* (2013.01); *G06N 99/005* (2013.01)

(58) Field of Classification Search
CPC .................................................. G06N 99/005
USPC ....................................................... 706/62
See application file for complete search history.

(56) References Cited

U.S. PATENT DOCUMENTS

| | | | |
|---|---|---|---|
| 5,931,763 A | 8/1999 | Alessandri | |
| 6,458,080 B1 | 10/2002 | Brown et al. | |
| 6,635,015 B2 | 10/2003 | Sagel | |
| 7,128,693 B2 | 10/2006 | Brown et al. | |
| 8,398,546 B2 | 3/2013 | Pacione et al. | |
| 2002/0107433 A1 | 8/2002 | Mault | |
| 2002/0156351 A1 | 10/2002 | Sagel | |
| 2003/0125983 A1 | 7/2003 | Flack et al. | |
| 2003/0208113 A1 | 11/2003 | Mault et al. | |
| 2005/0113649 A1 | 5/2005 | Bergantino | |
| 2006/0129432 A1 | 6/2006 | Choi et al. | |
| 2007/0136093 A1 | 6/2007 | Rankin et al. | |
| 2009/0281826 A1 | 11/2009 | Zak et al. | |

(Continued)

FOREIGN PATENT DOCUMENTS

| | | |
|---|---|---|
| WO | 0116855 A2 | 3/2001 |
| WO | 0139089 A1 | 5/2001 |

(Continued)

OTHER PUBLICATIONS

R. Bullough et al., "Interaction of Acute Changes in Exercise Energy Expenditure and Energy Intake on Resting Metabolic Rate", Am. J. Clin. Nutr., vol. 61, 1995, pp. 473-481.*

(Continued)

*Primary Examiner* — Kakali Chaki
*Assistant Examiner* — Vincent Gonzales
(74) *Attorney, Agent, or Firm* — Chiesa Shahinian & Giantomasi PC

(57) ABSTRACT

A health and fitness management system is provided that has a health and fitness application operating, e.g., on a smart phone, that can wirelessly communicate with an activity module worn on the user which has an accelerometer. The application accepts food and weight inputs (e.g., from the smart phone) and user activity units (e.g., from the activity unit) and develops a user intrinsic metabolism. The application includes fitness arc and health quotient graphical indicators that guide the user on health and fitness activities.

43 Claims, 23 Drawing Sheets

(56) References Cited

U.S. PATENT DOCUMENTS

| | | | |
|---|---|---|---|
| 2010/0211349 A1 | 8/2010 | Flaction et al. | |
| 2011/0087137 A1 | 4/2011 | Hanoun | |
| 2011/0106553 A1* | 5/2011 | Sato et al. | 705/2 |
| 2012/0268592 A1* | 10/2012 | Aragones et al. | 348/143 |

FOREIGN PATENT DOCUMENTS

| | | | |
|---|---|---|---|
| WO | 2006042420 A1 | 4/2006 | |
| WO | 2007001886 A2 | 1/2007 | |
| WO | 2009152608 A1 | 12/2009 | |

OTHER PUBLICATIONS

Bullough et al., "Interaction of Acute Changes in Exercise Energy Expenditure and Energy Intake on Resting Metabolic Rate," Am. J. Clin. Nutr., Mar. 1995, vol. 61, No. 3, pp. 473-481.

International Search Report and Written Opinion mailed May 22, 2013, in connection with International Patent Application No. PCT/US2013/021869, 27 pgs.

* cited by examiner

HEALTH AND FITNESS MANAGEMENT SYSTEM

CROSS-REFERENCES TO RELATED APPLICATION

The present application claims the benefit of priority to U.S. patent application Ser. No. 13/036,151, filed Feb. 28, 2011, the disclosure of which is incorporated herein by reference in its entirety for all purposes and as if completely reproduced herein including the accompanying claims and figures.

FIELD

The disclosed subject matter relates to a health management system, and to a system for managing the health and fitness of an individual.

BACKGROUND

Counting calories can be an inherently inaccurate process and cannot be successfully used to predict weight loss because food items and physical activity can be subject to wide variation, such as in relation to actual calories ingested or burned, e.g., from individual to individual, over time through life and even on a daily basis. Conventional weight loss programs often require the user to track food intake, which may be subjective. For example, one person's serving size for a particular food item may be different from another person's serving size. Moreover, weighing and measuring food items may be difficult to accomplish, and also difficult to do consistently over a course of a weight loss algorithm. In addition, tracking calories burned may be difficult, as the number of calories burned may vary from exercise to exercise and person to person.

As can be seen, for these and other reasons, there is a need for a more comprehensive health management system that is simple to use (i.e., to input food consumption and physical activity information), and that may adapt to an individual's particular and often changing response to certain food intake and exercise. Beneficially, such a system should also output metabolically related health parameters such as weight gain/loss, food quality, fluids intake and condition, salt intake and levels, percentage of vitamin rich foods, and, in addition, provide an overall health and fitness measurement that can be simply and readily understandable.

SUMMARY

According to one aspect, the described invention provides a fitness management method and apparatus comprises collecting food intake information for actual or expected food intake of a user over a first period of time and converting the food intake information into food intake units for the first period of time; collecting activity information for actual or expected activity by the user over the first period of time and converting the food intake information into food intake units for the user for the first period of time; collecting weight information representing a change in weight of the user over the first period of time; calculating, via a computing device, a calculated intrinsic metabolic rate for the user for the first period of time; collecting food intake information for actual or expected food intake of a user over a second period of time and converting the food intake information into food intake units for the second period of time; collecting activity information for actual or expected activity of a user over the second period of time and converting the activity information into activity units for the second period of time; calculating, via the computing device, a predicted change in weight for the second period of time based upon the calculated intrinsic metabolic rate for the user over the first period of time; collecting weight information representing an actual change in weight of the user over the second period of time; comparing the predicted change in weight for the second period of time to the actual change in weight for the second period of time; and determining, via the computing device, an updated calculated intrinsic metabolic rate for the user based at least in part upon the difference between the predicted change in weight for the second period of time and the actual change in weight for the second period of time. For example, the method and apparatus further comprise collecting food intake information for actual or expected food intake of a user over a third period of time and converting the food intake information into food intake units for the third period of time; collecting activity information for actual or expected activity of a user over the third period of time and converting the activity information into activity units for the third period of time; calculating, via the computing device, a predicted change in weight for the third period of time based upon the updated calculated intrinsic metabolic rate for the user over the first period of time; collecting weight information representing an actual change in weight of the user over the second period of time; and further updating, via the computing device, the updated calculated intrinsic metabolic rate for the user based at least in part upon the difference between the predicted change in weight for the third period of time and the actual change in weight for the third period of time. For example, the method and apparatus further comprise: displaying, via the computing device, at least one of an accumulation of food intake units and an accumulation of activity units over at least one of the first period of time, the second period of time and the third period of time. For example, the apparatus and method further comprise dividing the first period of time into a selected number of first sub-time periods; collecting food intake information for actual or expected food intake of the user over each of the first sub-time periods during the first period of time and converting the food intake information into food intake units for each of the first sub-time units during the first period of time; collecting activity information for actual or expected activity by the user over each of the first sub-time periods and converting the activity information into activity units for the user for each of the sub-time periods during the first period of time; collecting weight information representing a change in weight of the user over at least a last of the first sub-time periods and a first of the first sub-time periods to determine a change in weight of the user over the first period of time; dividing the second period of time into a selected number of second sub-time periods; collecting food intake information for actual or expected food intake of the user over each of the second sub-time periods during the second period of time and converting the food intake information into food intake units for each of the second sub-time units during the second period of time; collecting activity information for actual or expected activity by the user over each of the second sub-time periods and converting the activity information into activity units for the user for each of the second sub-time periods during the second period of time; and collecting weight information representing a change in weight of the user over at least a last of the second sub-time periods to determine a change in weight of the user over the second period of time. For example, the method and apparatus further comprise dividing the third period of time into a selected number of third sub-time periods; collecting food intake information for actual or expected food intake of the user over each of the third sub-time periods during the third period of time and converting the food intake information into food intake units for each of the third sub-time periods during the third period of time; collecting activity information for actual or expected activity by the user over each of the third sub-time periods and converting the activity information into activity units for the user for each of the third sub-time periods during the third period of time; and collecting weight information representing a change in weight of the user over at least a last of the third sub-time periods to determine a change in weight of the user over the third period of time. For example, the method and apparatus further comprise determining an updated calculated intrinsic metabolic rate for the user based at least in part upon the difference between the predicted change in weight for the second period of time and the actual change in weight for the second period of time and determining a further updated calculated intrinsic metabolic rate for the user based at least in part upon the difference between the predicted change in weight for the second period of time and the actual change in weight for the second period of time. A machine readable medium storing instructions that, when executed by a computing device cause the computing device to perform a fitness management method is disclosed in which the method for example comprises collecting food intake information for actual or expected food intake of a user over a first period of time and converting the food intake information into food intake units for the first period of time; collecting activity information for actual or expected activity by the user over the first period of time and converting the food intake information into food intake units for the user for the first period of time; collecting weight information representing a change in weight of the user over the first period of time; calculating a calculated intrinsic metabolic rate for the user for the first period of time; collecting food intake information for actual or expected food intake of a user over a second period of time and converting the food intake information into food intake units for the second period of time; collecting activity information for actual or expected activity of a user over the second period of time and converting the activity information into activity units for the second period of time; calculating a predicted change in weight for the second period of time based upon the calculated intrinsic metabolic rate for the user over the first period of time; collecting weight information representing an actual change in weight of the user over the second period of time; comparing the predicted change in weight for the second period of time to the actual change in weight for the second period of time; and determining an updated calculated intrinsic metabolic rate for the user based at least in part upon the difference between the predicted change in weight for the second period of time and the actual change in weight for the second period of time.

According to another aspect, the system of and method of the described invention comprises a food intake information and weight information input unit; an activity information collection and input unit separate from the food intake information and weight information input unit and adapted to move with a portion a body of the user. For example, at least one of the food intake information and weight information input unit and the activity information collection and input comprises the computing device. For example, the system and method comprises the food information and weight information input unit comprising a portable user device having a touch screen display. For example, the system and method comprise the activity information input unit comprising an accelerometer for detecting activity repetitions. For example, at least one of the food intake information and weight information input unit and the activity input unit, the computing device is configured to assign weighted values to each activity repetition according to one of the type and intensity of the activity and at least one of the repetitions detected. For example, the system and method comprise the food intake information input and weight information input unit further comprising the computing device configured to display a prediction of fitness performance based at least in part on a current metabolic rate for the user. For example, the current metabolic rate is computed by the computing device based on a difference between a predicted change in weight for a selected period of time and an actual measured change in weight for the selected period of time. For example, the displayed prediction comprises a graphical fitness prediction chart including perhaps a graphical fitness prediction chart.

BRIEF DESCRIPTION OF THE DRAWINGS

For a more complete understanding of the disclosed subject matter, reference can be made to the following detailed description of an exemplary embodiment considered in conjunction with the accompanying drawings, in which.

DETAILED DESCRIPTION OF EXEMPLARY EMBODIMENTS

Figure 1:
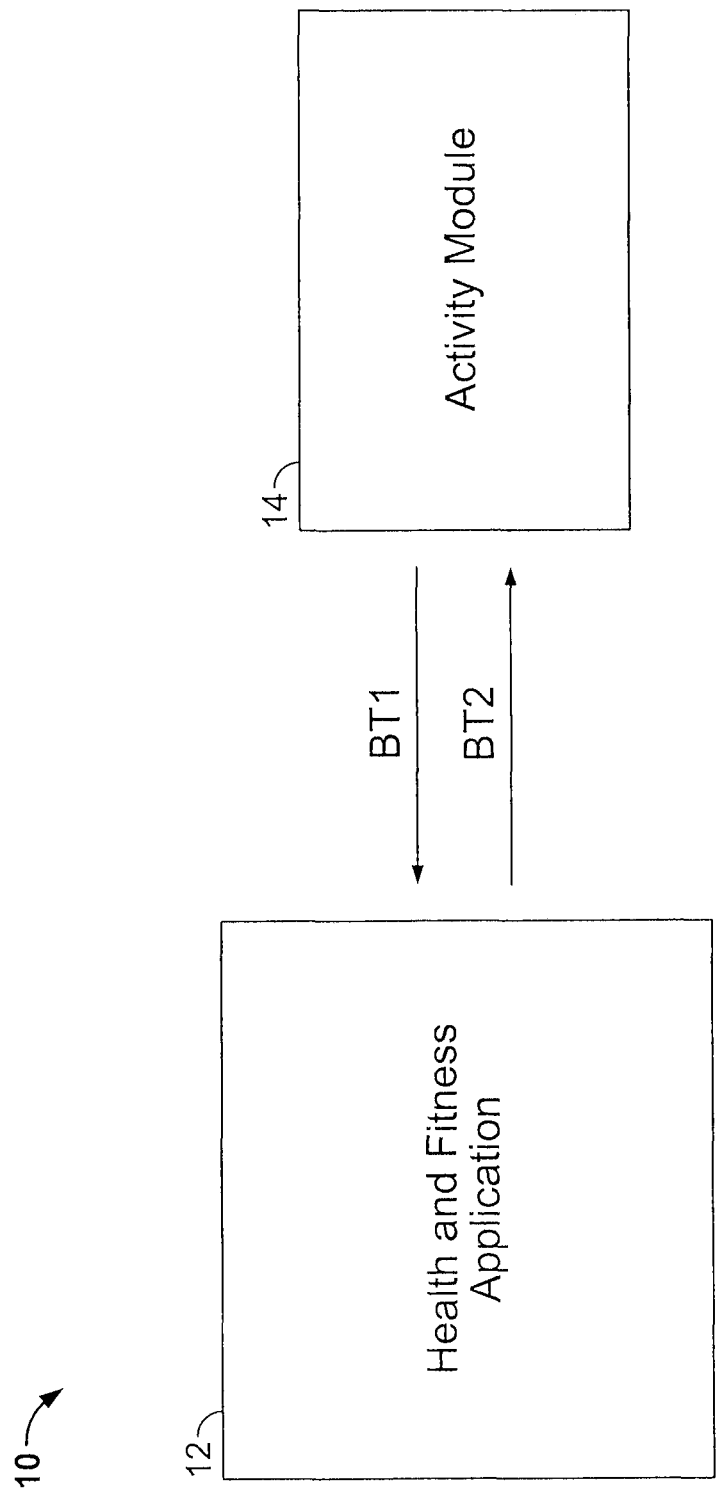
FIG. 1 is a schematic diagram in block diagram form of a health and fitness management system constructed in accordance with an exemplary embodiment of the disclosed subject matter, the system having a health and fitness application operating, e.g., on a smart phone, that can wirelessly communicate with an activity module.

The disclosed subject matter provides a health management system that includes an application that employs readily identifiable icons to facilitate the input of food consumption information, a motion sensor to autonomously facilitate the input of physical activity information, and the direct input of weight information into the application. The application utilizes the food consumption, physical activity, and weight input information to formulate and periodically adjust a resting or intrinsic metabolism for the user. The system provides instantaneous feedback on the relationship of food items and exercise to one's fitness level, including one's weight. The system does not require the user to count calories, either on the intake or expenditure side of the weight management paradigm. Rather, the system employs icons and graphic displays, without units, to provide a user-friendly interface. The health management system can also integrate weight, food intake and physical activity and can learn the individual's unique response to each element to predict the direction of weight gain or loss.

In an embodiment, the system includes a digital device such as a smart cell phone or tablet device which, for example, may employ an Android operating system. The device runs a software application including algorithm code adapted to i) receive an input corresponding to the calories consumed by the user via a graphical representation of the food portion that can be graphically adjusted by the user, ii) receive an input corresponding to physical activity of the user via wireless transmissions by a motion sensor worn by the user, and iii) receive an input corresponding to weight of the user via direct input by the user. The application predicts the user's fitness level and intrinsic metabolism based on the input corresponding to calories consumed and the calculation of calories burned due to activity, and adjusts the user's fitness level prediction based on historic measurements of the calories consumed, the calories burned, and the weight of the user. The application also uses the data to predict what can happen to the user's weight based upon the real time assessment of caloric needs. The application provides graphics which can be updated at predetermined intervals, such as every ten minutes, to reveal fitness parameters including the user's daily overall energy balance.

There can be, by way of example, four components or parameters that can be used by an algorithm in the system. Briefly, the components can be calories consumed, calories burned through activity (e.g., exercise), weight, and the calories necessary to maintain basic physiologic function or intrinsic metabolism. If three of these parameters can be known, then the fourth can be derived via an energy balance calculation. Therefore, formulating the intrinsic metabolism requires registering the calories consumed, and monitoring and assigning caloric value to physical activities. The energy balance calculation is disclosed in greater detail hereinafter.

FIG. 1 illustrates a health management system 10 ("the system") which can be constructed in accordance with an exemplary embodiment of the disclosed subject matter. The system 10 can include a health and fitness application 12 ("the application") and an activity module 14. The application 12 can communicate wirelessly with the activity module 14, e.g., via Bluetooth™ or other ad hoc local wireless node transmission, e.g., over channels BT1 and BT2. The activity module 14 can be worn by the user, for instance when he/she exercises, to measure and wirelessly transmit activity units accumulated during exercise, to the application 12. The application 12 can, by way of example, convert the activity units into calories burned during exercise (i.e., in addition to the calories burned by intrinsic metabolism).

Figure 2:
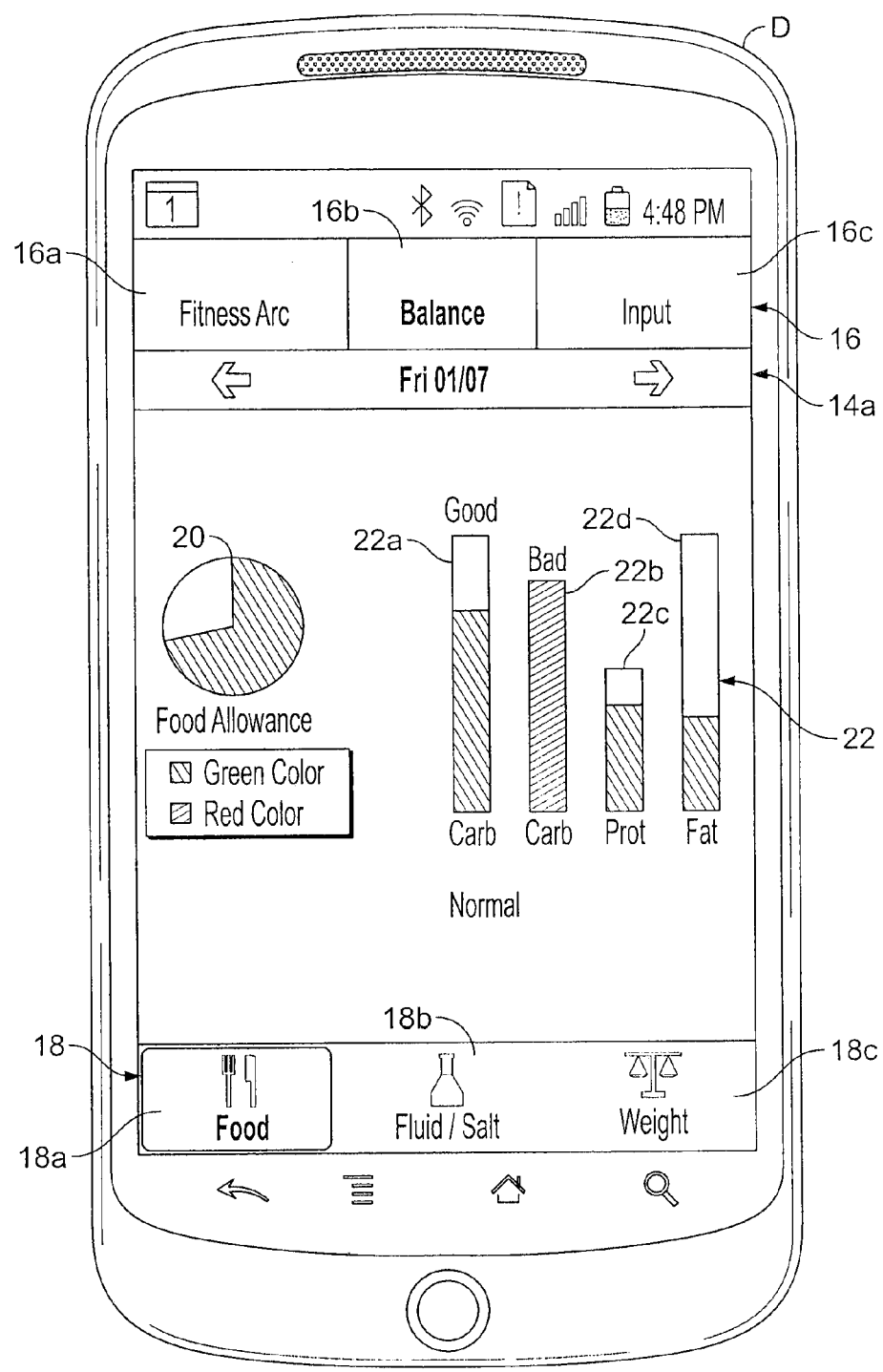
FIG. 2 is an illustration of a food circle information screen on the smart phone that can be provided by the application.

Referring to FIG. 2, the application 12 can be adapted to run on a digital device D such as a smart phone, tablet computer, or conventional personal computer, such as a desktop or laptop computer. In an embodiment, the digital device D may run a Smartphone based operating system. Alternatively, the application 12 may be employed on a stand alone device such as a wrist-watch like device or other digital device (not shown) that can be specifically adapted to provide the functionality described in the present patent application.

The application 12 can include a plurality of software algorithm codes for displaying data, calculating data, receiving data and the like. When the software can be run on the digital device D, buttons such as primary input buttons 16, 16a-16c and secondary input buttons 18, 18a-18c may be displayed. The buttons 16, 16a-16c and secondary input buttons 18, 18a-18c may be touch pad input buttons when the digital device D includes a touch screen. In another embodiment, a graphical user interface, such as a mouse with a selection button(s) (not shown), e.g., the right or left key selection button on the mouse, may be used to navigate an icon about the screen of the digital device D and the selection button may be used to select one or more buttons 16, 16a-16c and secondary input buttons 18, 18a-18c, e.g., by clicking on such button representations of the screen or icons or the like.

Selected buttons 16b, 18a may be highlighted on the screen. In this case, the primary input button 16b for "balance" and the secondary input button 18a for "food" may be selected. In an embodiment, the button 16b for balance provides the following three secondary button options which can then be icons or button representations, e.g., positioned at the bottom of the screen as illustrated in FIG. 2. The options are briefly described below followed by more detailed disclosures in the present patent application.

The Food Tab/Button:

As depicted on the screen of the digital device D as shown in FIG. 2 a food circle 20 can be used to represent an allowed daily amount of food, e.g., that can be necessary to maintain a current weight of the user. It can be color coded, e.g., filled with green color which can turn red, e.g., as the user adds more food than allowed. It can be understood that colors described herein can be depicted as fill-patterns in the figures. Although the color code for the fill-pattern can be shown on FIG. 2, the code can remain the same for all figures in the present application. It can also be understood that any graphical element (e.g., food circle 20) that fills with the color red will also be accompanied by a message that will be displayed (not shown) which will described the impact of that color change on the relevant physiologic function. The amount of food required to fill the food circle 20 can be specific to each individual and can also vary with certain factors, such as the amount of activity the user performs. For example, if the food circle (pie chart) 20 can be red or partly red, the user should be gaining weight for that day and in proportion to the amount of the food circle 20 that can be showing red as opposed to green. The user can change color back to green, e.g., by doing more physical activity.

Figure 3:
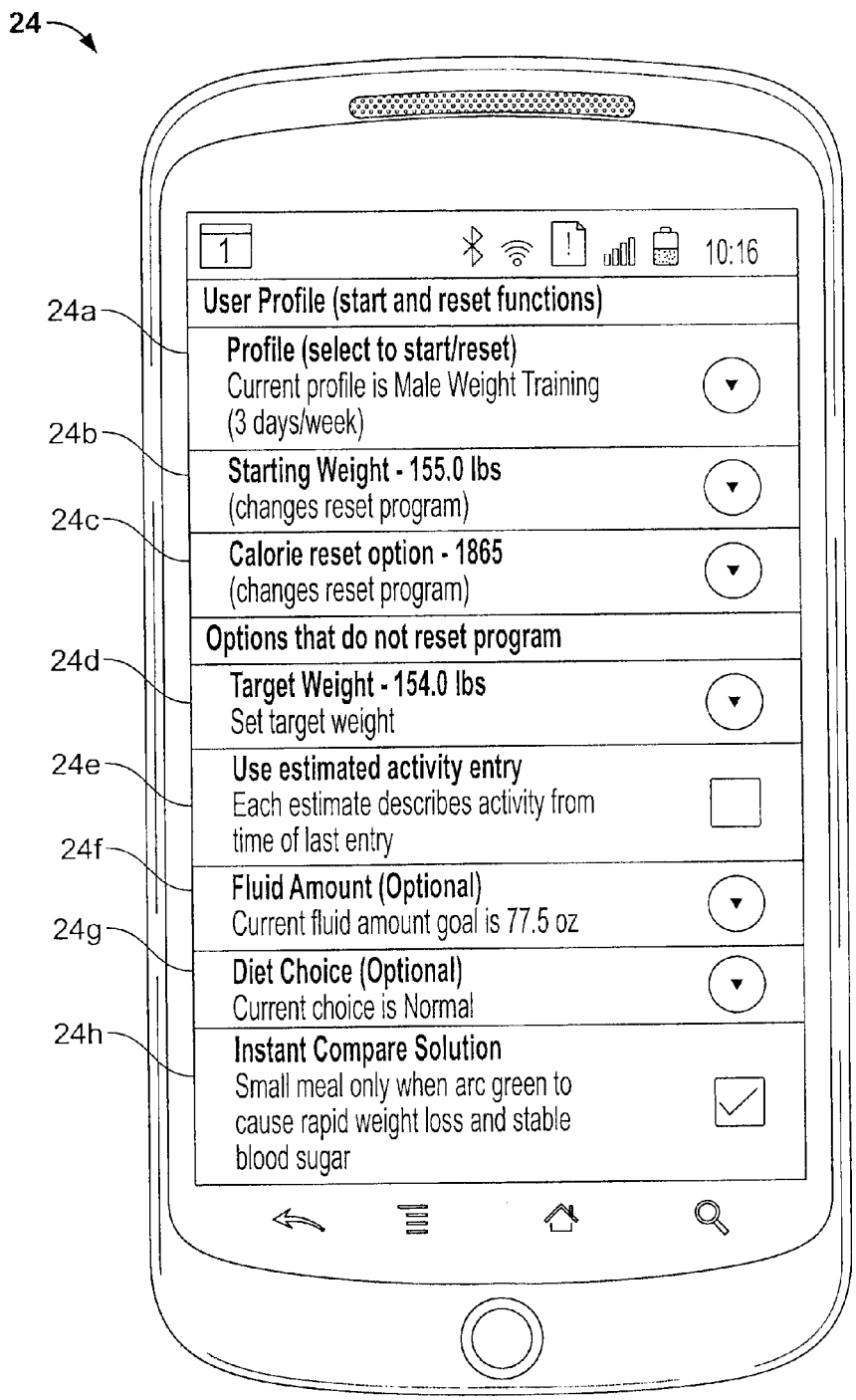
FIG. 3 is an illustration of a user profile input screen on the smart phone.
Figure 4:
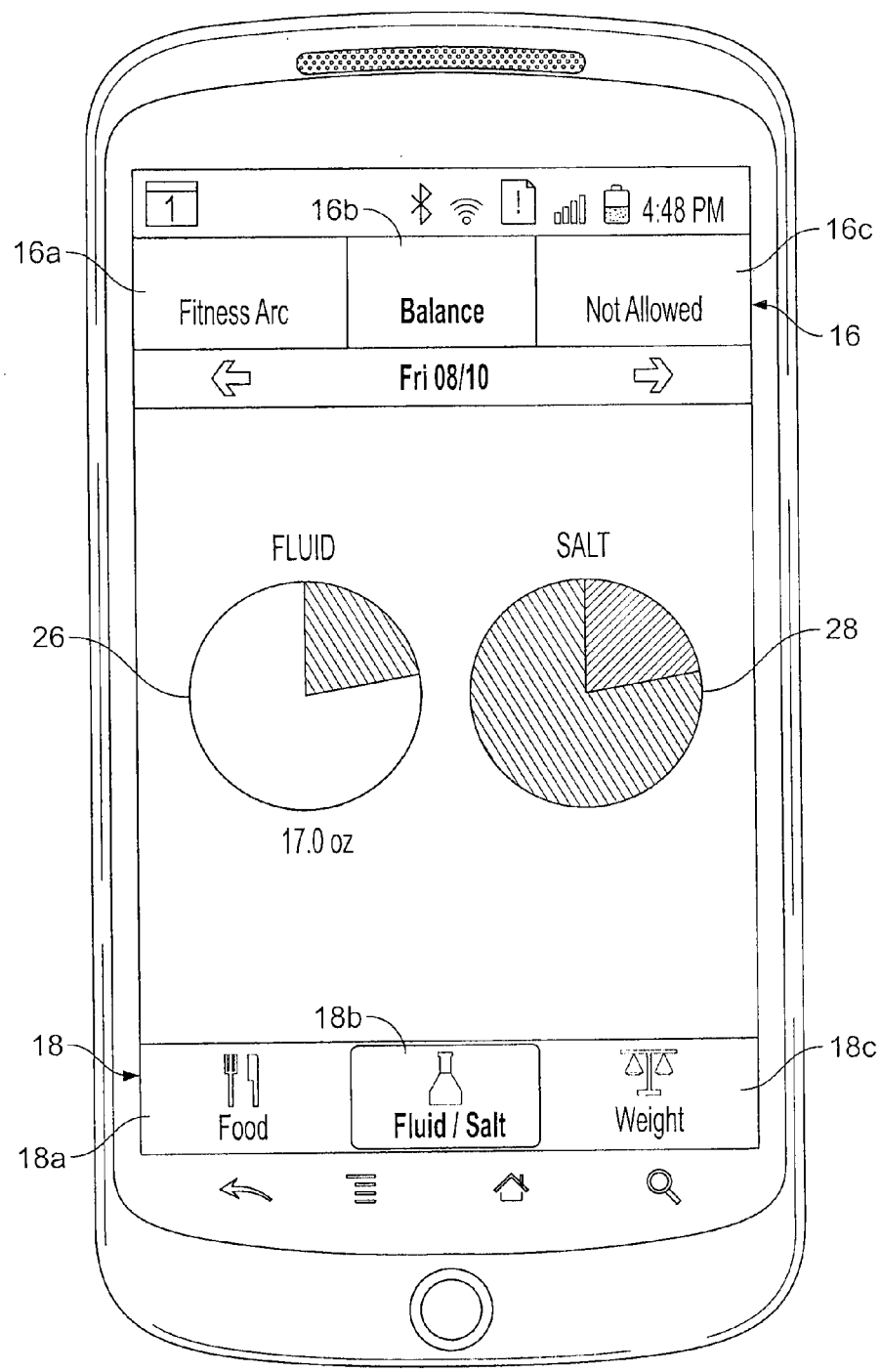
FIG. 4 is an illustration of a fluid and salt circle information screen on the smart phone.

Fluid/Salt Tab or Button 18b:

As depicted on the screen of the digital device D as shown in FIG. 4 fluid and salt circles 26, 28, respectively can be used to indicate a daily 26 allotment amount in circle 26, which may be determined from an estimated daily fluid consumption goal, which may be input by the user on field 24f, e.g., as depicted on a profile page 24 depicted in FIG. 3, discussed in more detail below. Actual fluid consumption can then be input by the user throughout the day. The salt circle 28 can fill, e.g., as dietary choices can be made throughout the day. Green can then be used to represent that the user can be consuming or has consumed salt in a manner that can be, e.g., consistent with current dietary recommendations. In an embodiment, if the user exceeds recommended salt allowances as the day progresses, the color can progressively change, e.g., to yellow, as indicated by the no cross-hatching for red shown in FIG. 2 and then red as the user inputs his/her food consumed.

Figure 5:
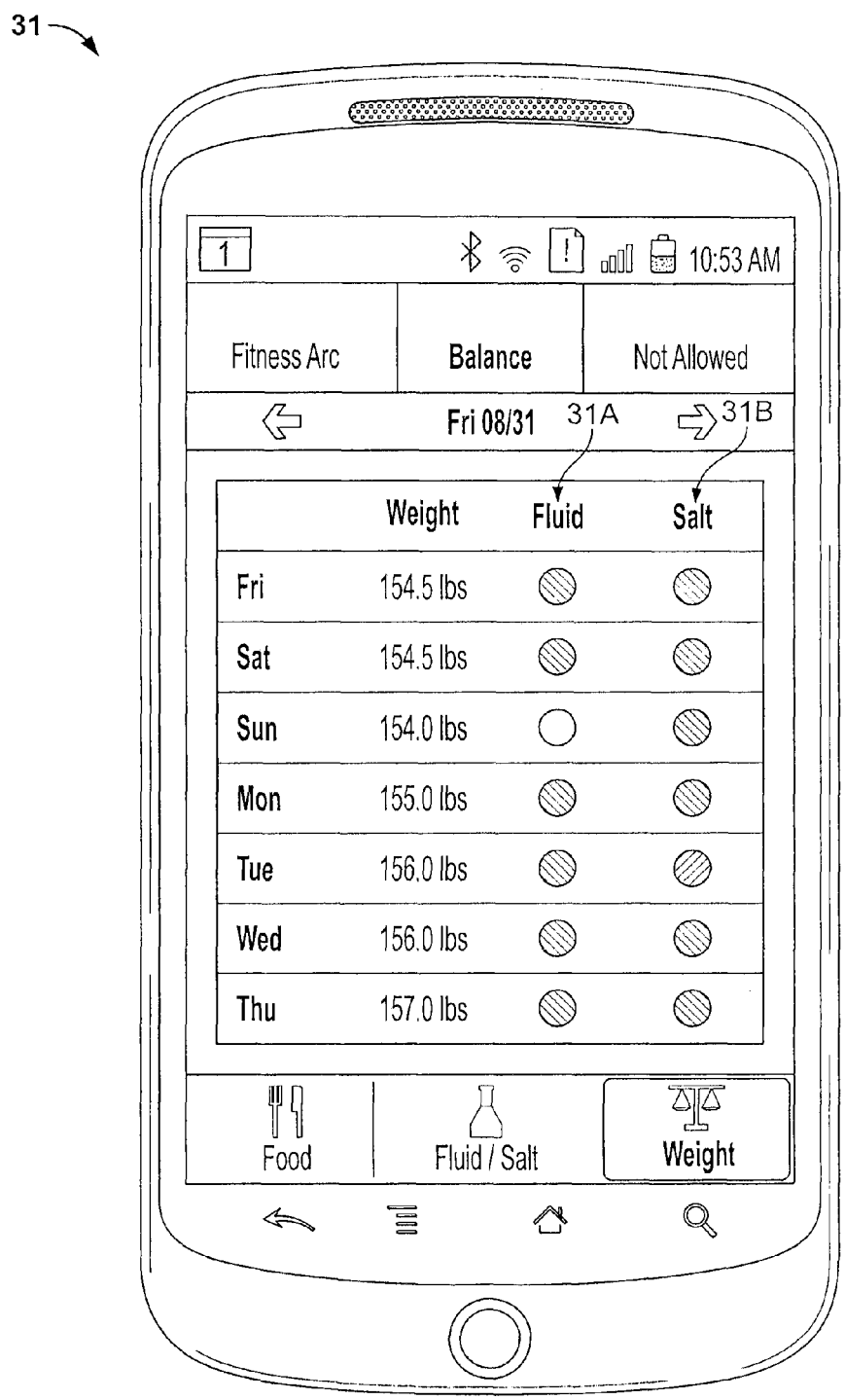
FIG. 5 is an illustration of a weight related to fluid and salt information screen on the smart phone.

Weight Tab/Button 18c:

As depicted on the screen of the digital device D as shown in FIG. 5, the device includes weight information, e.g., on a daily basis, and associated proportional fluid 31A and salt information 31B. Green indicates compliance with health and fitness guidelines, yellow indicates excess, and red indicates overly excessive (e.g., unhealthy) consumption. In an embodiment, previous weeks can be reviewed by tapping the left return arrow 33 on the date bar to move for display on the screen of the prior weeks and the right advance arrow 33 to move forward in time back to the current week.

As disclosed in more detail below, the application 12 can convert iconic food items input by the user into a numeric figure which, as an example, over time may be learned by the system, e.g., by derivation from an analysis of previous food selections and their impact on weight when also, e.g., compared with the user's actual and historic activity level and when referenced against the calculation of intrinsic metabolism by the system 10. The intrinsic metabolism may, by way of example, be held as a constant until it can be determined by the system 10 that this value for intrinsic metabolism no longer correctly predicts the direction/amount of weight gain or loss. At such time the system 10 may recalculate the value for intrinsic metabolism and retain it as the present constant, e.g., so that the instantaneous energy balance of the user can be calculated and displayed on a user friendly and readily identifiable graphic, as can be shown, by way of example in a fitness arc 34 in FIG. 6.

Referring back to FIG. 2, in an embodiment, graph 20, as illustrated as a circle graph, can be used to display allowed food intake and actual food intake, respectively, for a given day. For example, circle graph 20 may indicate that the user's total food intake for the given day can be less than the maximum prescribed, e.g. as indicated by the portion of circle graph 20 that can be white (no cross-hatching, e.g., indicating the food intake can be about 30% below recommended), or can be on target, e.g., if the green color increases to fill the entire circle (not shown in FIG. 2,) or can be "excess," e.g., by the portion that can be in red, that is not shown on the circle graph 20, but can be imagined as the white portion becoming green. This would then indicate, as an example, that the food intake was about 30% in excess.

As noted above, the circle graph 20 can be, e.g., a proportional representation of the way in which the user's daily food consumption has been distributed between the major food groups, and this can be calculated by the application 12. The circle graph 20 may show one color for food caloric intake (for example, a white background changing to green as calories are consumed), the background color also showing the food units remaining, which if consumed to the allowed amount can result in the user reaching the pre-selected weight goal (the white color remaining), and another color, e.g., red when caloric intake exceeds the allotted calories for the given time period. The graphic allowance for food intake can be adjusted to the user's activity level each day, so that, if the activity level increases above the expected, an adjustment can be made which can, e.g., allow more food to be entered before the food circle 20 can be completely filled.

In an embodiment, the bar graphs 22 may be utilized to further break down various food intake categories into separate graphs. For example, carbohydrates (carbs) may be broken down into bar graphs on good and bad carbs 22a, 22b, respectively, and protein and fat may be displayed on graphs 22c, 22d, respectively. Allotments (i.e. how much room there can be to fill the graphs for each food type) depend on the diet which can be input by the user in field 24g of the profile page 24 depicted, by way of example, in FIG. 3. If the user changes his/her diet, the bar heights for each of the food groups can also change. The graphs 22a-22d may be useful for persons on a low fat or a low carb diet. The graphs 22 may be color coded, as noted above as an example. For example, the good carb 22a, the protein 22c and fat 22d graphs may be partly green on a white background, to show that the daily allotment has not yet been consumed, but the bad carb 22b graph may be changed to completely red, showing that the daily allotment has been exceeded, or as noted above with the circle graph of FIG. 2, may change to red on the green background when and to the degree that excess bad carbohydrate intake is increased above the recommended level. The percentages of food type can be assigned by the application 12 so that the user only selects the iconic representation of the food item (i.e., during food consumption estimation inputs, as discussed in more detail below), and the application 12 can then determine the percentages of each elemental food type (i.e., protein, fat, carbohydrate, as well as salt content) that can be contained therein.

The actual allowed amount of food type which can be permitted before the graphs 22a-22d can completely fill in over the initial background color and change color can be determined by the allowed food amount, which can be determined, e.g., by the application 12 and the diet type selected by the user or health advisor, e.g., as input on a user profile screen 24 shown in FIG. 3. More particularly, with reference to FIG. 3, in an embodiment, the user profile input screen 24 can be employed to initially set up, as well as change, parameters such as Profile 24a (user sex, type and frequency of exercise training, etc.), Starting Weight 24b, Calories 24c (daily consumption objective), Target Weight 24d, User Estimated Activity 24e (estimate of number of user activity units, as described below), Fluid Amount 24f (amount of fluid desired to be consumed daily, in ounces). The fluid amount may be determined, e.g., by the user's weight, but the targeted amount of fluid to be consumed can be adjusted, by way of example, at the user's/health advisor's discretion. The color coding for fluid, in an example, may not attempt to target a minimum or maximum allowance, but may simply allow the user to track the volume of fluid consumed. The target for salt consumption may, e.g., track standard daily sodium content recommendations. In some cases, this may not be open to adjustment by the user. The user profile input screen 24 can also include parameters such as Diet Choice 24g, and an Instant Compare Option 24h (which can allow instant input of activity units in the application 12, as opposed to an input in the application 12 that attempts to replicate normal metabolic changes, e.g., every three hours, thus permitting the user to gain instant access to the impact of his/her activity units).

In an embodiment, the system 10 normally can be employed using some or all of the features described in the present application in connection with the application 12, e.g., while operating in conjunction with the activity module 14 (i.e., operating in a "combined mode"), or in a mode in which all the features described herein in connection with the application 12 can be operating without inputs from the activity module 14 (i.e., "the estimated mode"). The application 12 can be switched back and forth between the estimated mode and the combined mode on the user profile input screen 24 by checking or unchecking ESTIMATED (not shown in FIG. 3). For example, the user may elect i) to not wear the activity module 14 at all during a particular day, ii) or to just wear it for exercise only on a particular day, in which instance the estimated activity can be entered just before beginning the exercise. The activity accumulated by the activity module 14 can be downloaded after the exercise.

Referring to FIG. 4, in an embodiment, when secondary input button 18b "fluid/salt" can be selected, the user can observe during the day his or her progress with fluid and salt intake, as it relates to the objectives established in the user profile input (i.e., see FIGS. 3, 24f and 24g). In an embodiment, the progress may be shown on fluid and salt circles 26, 28, respectively. The fluid and salt circles 26, 28 may be color coded to help reveal desired intake, current intake amount remaining or in excess of recommendation. The circle graphs 26, 28 may also be helpful, for example, in monitoring salt intake for users on a salt-restrictive diet. In addition, fluid/salt progress indicators can be associated with weight on a weight summary screen 31 which can be described below.

FIG. 5 illustrates a weight summary screen 31 listing the daily weight history and associated fluid and salt color coded indicator circles 31A and 31B, respectively, for the current week. Each food item can be assigned a salt value and serve to fill the salt circle 28 as a percentage of food units calculated by the application 12, such that the higher the percentage of the high salt foods, the fewer food units can be needed to be consumed to fill the salt circle 28. The fluid circle 26 depicted on FIG. 4 fills as liquids can be selected. The fluid and salt circles 26, 28 or representations of them can populate the listing 31 to help the user analyze the effect of fluid and salt on weight.

Figure 6:
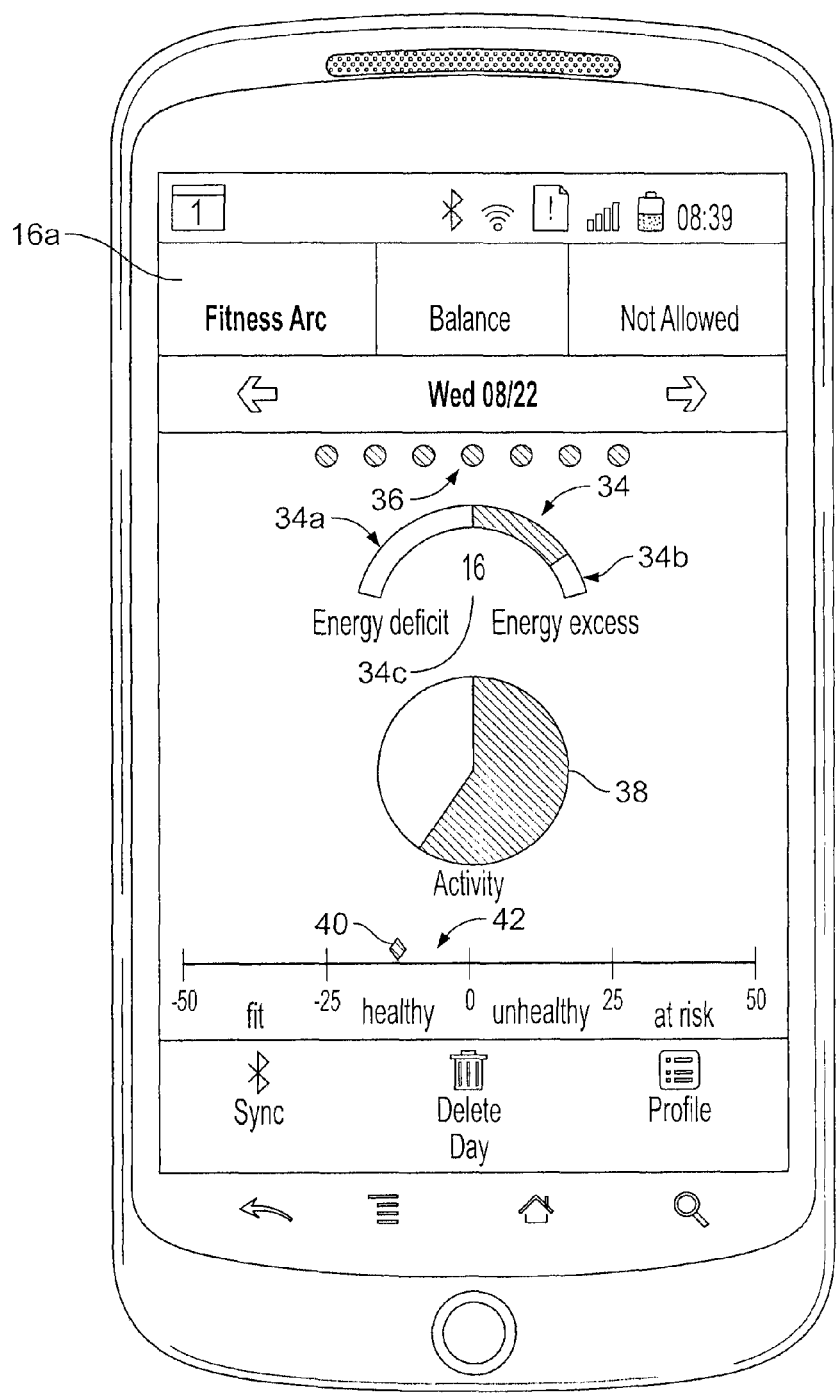
FIG. 6 is an illustration of a fitness arc information screen on the smart phone.

Referring to FIG. 6, the results of the energy balance calculation can be presented graphically on the digital device D screen, e.g., as a graphical fitness arc 34. The fitness arc 34 can be utilized to depict a measurement of daily energy balance and provide a daily indicator of fitness and health. In an embodiment, the accuracy of the fitness arc 34 can be enhanced by the application 12. More particularly, the application 12 can, e.g., periodically recalculate the user's intrinsic metabolism to provide an energy balance correction. Every person has a unique and changing metabolism such that consumption of similar quantities of food and similar amounts of activity can have different effects on the weight of the user, which weight can be utilized as a fitness indicator. Thus, there can be a different amount of remaining energy units available every day for storage as fat and therefore different consequences to weight in different individuals. This discrepancy can occur even if activity and food consumption can be identical. This constitutes the meaning of intrinsic metabolism according to the presently disclosed subject matter. These parameters can be continuously varying, i.e., they can be constantly changing with resultant different effects on weight for any individual user. The application 12, by monitoring its ability to predict weight based upon the activity units and food intake input, can constantly vary the allowed food intake should the application fail to accurately predict the change in the weight of the user. Thus, the continuous variable of intrinsic metabolism can, as an example, constantly be adjusted to correct for changes in the rate of energy consumption as fitness levels change or as food consumption and activity patterns change. By adjusting the metabolism calculation the application 12 can, e.g., determine modified food allowance(s) to match changes in activity.

The application 12 by way of example, can work without a requirement that the food input from the user be accurately reflective of the actual calorie content of food consumed. The application 12 only requires that the user have a reasonably similar pattern of icon use to describe food intake. For example, a sandwich eaten on one day may be bigger or smaller than the same eaten the day before, but the system does not require the user to actually reflect the absolute caloric content consumed. The algorithm can, by way of example, learn the way the user describes food and then assign a food unit value to each food component, e.g., contained within the sandwich, based upon an algorithm utilized by the application 12. In this manner, any habitual over/under food portion estimation(s) by the user can be detected and compensated for, thereby facilitating the application 12 in maintaining or reaching a user's target weight goal as specified in the user's profile (see FIG. 3, 24d).

Continuing to refer to FIG. 6, when primary input button 16a, "fitness arc" can be selected, a color coded energy deficiency/energy excess fitness arc 34 can be displayed on the display screen of the digital device D. In an embodiment, the fitness arc 34 can be formed in a semi-circular shape, where one side of the semi-circle can be an energy deficit portion 34a (i.e., indicative of weight loss) and the other side of the semi-circle can be an energy excess portion 34b (i.e., indicative of weight gain). In an embodiment, a red color may show when the energy deficit 34a can be present for that particular moment of the day (e.g., within periodic updates, such as, 10 minute updates), and a green color may show when the energy excess 34b can be present for that day. The portions 34a, 34b of the fitness arc 34 can change throughout the day, depending on the user's indicated physical activity and indicated food consumption. In an embodiment, coincident with the update of the fitness arc 34, a fitness arc value 34c can also be displayed. This value can represent the delta or change in fitness arc 34 units with each periodic, e.g., 10 minute interval, e.g., plus for an increase in energy excess (the body can be consuming energy through activity at a higher rate than necessary based on indicated food intake and the current intrinsic metabolism of the user) and negative for an increase in energy deficit (the body can be consuming energy through activity at a lower rate than necessary based on the indicated food intake and the current intrinsic metabolism of the user). At the conclusion of each day, the fitness arc 34c final value can be displayed. It can also be understood that the value for the fitness arc can be normalized and the color coded indication on the arc 34 used to indicate the positive or negative state of the energy consumption.

The fitness arc 34, therefore, can be used to visually inform the user as to the effect of the real time food consumption of the user referenced against the real time analysis of the actual physical activities of the user. At any given point in the day, the actual activity units and their impact on the fitness arc 34 can then be referenced against expected or historic levels of activity for that same time of the day. The fitness arc 34 displays can be adjusted based upon what can be expected and what has occurred. Activity units can be measured and assigned a value based upon the currently determined value for the calculated intrinsic metabolism of the user. The activity unit's value can be then used to calculate the energy balance that also can then be used to predict weight gain or loss, even before the food consumption or activity can be carried out.

Thus, given the inherent variation between each individual's rate of intrinsic metabolism and the manner in which he/she describes the food with the available icons, and/or activity input, each user can have different food unit values assigned to the same indication for a food item(s). The effect of activity on the balance of energy can be calculated, not directly against the food unit intake but it can be first processed, by the application 12, through a separate algorithm, e.g., imbedded in the calculation of the intrinsic metabolism. Thus neither food nor activity directly affects the energy balance or fitness arc 34, but can be instead analyzed based upon their historic and/or learned impact on intrinsic metabolism. The application 12 thus can create an ongoing user profile of intrinsic metabolism, activity, and food choice/amount that can be unique to each user. In an embodiment, the various components of application 12 may be calculated periodically, e.g., at 10 minute intervals, although other intervals can be also applicable. In an embodiment, it may take the application 12 about two weeks to define and calculate the user's metabolic profile and assign the values to his/her activity units and food intake units. It can be understood that such analysis can be further refined and adjusted by the selection of a target weight by the user. The algorithms, programs, or calculations underlying the behavior of the fitness arc 34 are described in greater detail below.

As disclosed above, the four components or parameters used by the algorithms in the application 12 can be indicated food intake (and, thus, apparent calories consumed), indicated type and amount of activity, i.e., exercise (and thus, apparent calories burned through activity), weight, and finally the calories necessary to maintain basic physiologic function, i.e., intrinsic metabolism. The application 12, therefore, can begin a monitoring process by assigning a value to each of the four parameters and running a series of daily calculations to determine the accuracy of the assigned values in relation to one another. The accuracy can be determined, by way of example, on the ability for one set of assigned numbers to accurately predict the others. Based on a weighted numerical coefficient of each data point which can, e.g., vary at specified times of the day and week, the algorithm can, e.g., choose three of the four definable parameters and then calculate the fourth variable, e.g., for one, some or all of the variables.

If the algorithm fails to predict the fourth value accurately, where accuracy can be defined in such a manner that, e.g., if the calculated variable can be reinserted into the application 12, the application 12 accurately predicts the parameters that can be measured at that time, which can be seen as confirming the accuracy of the calculated variable, then new values may be assigned, e.g., to the other variables, and the calculation redone until each variable accurately predicts the others when inserted into the algorithm of the application 12. The variables chosen for analysis may also be seen and learned to vary at different times of the day or week and the application 12 suitably varied to specify that the value can have the greatest accuracy relative to the other values according to the learned/determined variability. This recalculation may also include actual weight which can be directly measured.

The most complicated of the calculations may often be determined to be that of the intrinsic metabolism for a given user. In this case, there may be no direct measurement and thus the value can be, of necessity, a derived value, which may also vary from user to user and for a given user over time and in many cases according to one or more variables, e.g., daily, weekly, monthly, seasonally, time of day, exercise schedule and the like. This changing variable for intrinsic metabolism can be, e.g., derived from the dynamic interplay of the measured/indicated variables, which can be, e.g., first referenced against, e.g., the predicted value and/or actual value of each parameter. As data about the individual user can be collected, the learned allowed variance between measured variables can be narrowed. The intrinsic metabolism can be calculated and held as a constant.

However, the intrinsic metabolism may be, e.g., held as a constant only for a prescribed period and recalculated as metabolism for the user changes. In other words, if three of the variables can be measured and a rate of change in weight calculated, a constant can be calculated for the intrinsic metabolism. The constant for intrinsic metabolism currently calculated can then be used to predict weight given the indicated activity and indicated food intake. Should the algorithm fail to accurately predict weight given the indicated activity and food intake for the user, then the constant for intrinsic metabolism can be changed. When the constant for intrinsic metabolism can be found to perform adequately in the algorithm of the application 12, the algorithm can maintain the use of the constant and predict, e.g., using changes in either indicated activity or indicated food intake to predict a cumulative impact on fitness, e.g., as measured by change or lack thereof in weight. The algorithms of the application 12 can then be used to study the relationship between the two ongoing variables, indicated activity and indicated food intake, and combine the variations simultaneously and contemporaneously to each other so that, as an example, as one varies, the other can be determined even without the necessity of direct and absolute measurement for the variable, i.e., in such a way that if the user were to actually consume the entered indicated food intake and/or were to actually perform the indicated/entered number of activity units, then the user's weight would remain unchanged. In other words, the algorithm for the application 12 can adjust to inaccuracies in the indications of the food intake and/or activity level, which, if consistently entered by the user and/or determined by the system 10 from inputs from the user or inputs from a component in the system 10 itself, can still determine a constant for intrinsic metabolism and other metabolic activity of the user so as to accurately predict change in fitness over time, as indicated, e.g., by change in the weight of the user.

The display in the fitness arc 34, by moving in the left or right portions, can be seen to denote how far the user can be from good fitness behavior, e.g., as indicated by weight neutral behavior. The fitness arc 34 scale can be set so that if the combination of indicated food consumption and indicated activity performed produces a full energy excess red arc portion 34b for a given period of time, e.g., for seven days, then the user can have gained a predictable amount of weight, e.g., at least one pound, in that given period of time, e.g., one week. If the combination of indicated food consumed and indicated activity performed produces a full energy deficit green arc portion 34a, again for a given period of time, e.g., for one week, then the user can have lost the predicted at least one pound in that week. In this way fashion, an accurate prediction of weight change can be maintained, e.g., as long as the intrinsic metabolism of the user and the user's pattern of identifying indicated food intake and/or indicated activity type and amount also remain the same or essentially so.

Variations in indicated food intake versus indicated activity, therefore, can then be used to inform the user as to the expected affect on weight as well as on an overall health quotient 42, as discussed in more detail below. With variation in indicated food intake and/or indicated activity, either due to change in behavior by the user or change in the way of inputting the indicated behavior of the user, e.g., vis a vis food intake and/or activity, on a more or less real time basis, the system 10 can advise the user as to how much variation in the one or the other can be needed to achieve a certain weight.

Should the application 12 then show an indication(s) that it cannot make such predictions accurately, e.g., the constant (i.e., intrinsic metabolism) can be recalculated and/or new values can be assigned to an indicated parameter(s) so that they can be weighted in a way that accounts for the observed variability, leading from, e.g., a user's over or under indication of real food intake and/or real activity. By way of example, the greater the variability of the user inputs from the reality of the food intake and/or activity, the greater can be the value for the derived increase or reduction in the weightings assigned to that value in the calculations by the algorithm. In other words, the intrinsic metabolism can be a constant derived from measured values (as a function of user input, e.g., for food intake and activity) which themselves can be defined by tolerance parameters assigned by the application 12 itself, e.g., referenced against actual indicated weight change, and the currently determined constant for the intrinsic metabolic rate of the user.

In an embodiment, the fitness arc 34 can be used to depict the relationship between two power equations. The first power equation, e.g., can measure the rate of energy transfer, and the second power equation, e.g., can measure the movement of a fixed mass over a specified distance per unit time. The relationship expressed in the fitness arc 34 can be, e.g., a percentage change between the expected and observed value of each power equation. The percentage change of each equation can be given a weighted value and then the two can be summated to produce a graphic representation, e.g., of relative change against an absolute weight unit. The first and second power equations are discussed in more detail below.

Power Equation 1

In power equation 1, power P can be defined as the rate at which energy can be transferred or consumed, and food units can be calculated, e.g., to be user specific, as units of energy taken in by the user. Another way to express this can be the familiar "calories in vs. calories out." Once calculated, food units and energy used units can form the basis upon which a metabolism for the user for a given level of indicated activity undergoes an update as to the rate at which the user actually consumes the indicated amount of intake of food units. The food units can be seen as energy equivalents which can have different values for different foods, types of food and even different users. Food unit values can then be assigned, e.g., by the ability of a given indicated value for the food unit(s) to effect weight, and not by an absolute caloric amount. These food units may be, by way of example, assigned an initial value based upon a published caloric content. The algorithm of the application 12, can then reassign a value(s) to some or all indicated food(s) intake(s) periodically, e.g., on a weekly basis, e.g., based on how the food(s) affects the weight of the user.

The application 12 may do this, e.g., by maintaining ratios of initial assigned food values versus learned/established value(s) such that the ability to affect the weight of the user as determined from the current value for the intrinsic metabolism for the user and the indication(s) of food intake by the user can be used to determine a value for a food unit. Thus an extra 3500 calories (i.e., the number of calories required to gain one pound) may be more or less than the food units as used by the application 12 to change and/or predict a change in the weight of the user by a given amount, e.g., by one pound. Once the value of energy can be assigned to a food unit, as an example, a weekly allotment of food(s) can then be used to determine the ratio of the food units (e.g., calories) of the food(s) to the food units used by the application 12, and can be extended to all food analyzed by the application, at least as a starting value, regardless of whether or not that particular food has been consumed and thus previously analyzed by the intrinsic metabolism calculation.

Power equation 1:
$$\text{Power } P = E_t$$

where $E_t$ is the energy transferred to the user from that stored in food units indicated to be consumed by the user to the energy needed to be used up (indicated to the system 10 to be used up or predicted by the system 10 to be used up, by the user (over some period of time) in order to maintain the total metabolism of the user (including the current constant for intrinsic metabolism of the user) so that there can be no change in weight during a given period of time, e.g., in the course of one week. It can be understood that this may be expressed as a ratio of energy in to energy out (user total metabolism) or the ratio of energy in to the energy consumed by the excess activity of the user over and above the intrinsic metabolic rate of the user.

The rate of energy transfer can be estimated from the rate at which weight can be gained or lost. The unit of energy can be defined, e.g., by the number of food units necessary to maintain a stable body weight, given an indicated level of energy used by the user in the course of activity by the used as indicated by the type and amount of activity input by the user and the activity module, as discussed in more detail below. In an embodiment, the food unit energy value can be established by determining how many food units can be consumed over a period of time, e.g., one or two weeks in which there can be variability in weight. The variability in weight can then be referenced against the variability in food units taken in to determine the number of food units which would result in a change of one pound in weight, also referenced to indicated activity level(s).

As an example, the number of food units minus the number of food units attributable to the addition of one pound can be identified by the term "expected value". It can be understood that the same estimation can be made for a pound of weight that can be measured to be lost. The "expected value" can be the number of food units that, for the specified time of the day, and the actual/predicted activity level(s) the application 12 anticipates the user can consume. If the "expected value" can be consumed in each interval (and the activity units described below can be known/predicted, e.g., held constant), the user can maintain weight neutrality over the course of the given period of time, e.g., one week. The 10 minute processing of the relationship between the expected and the observed can then be displayed in the fitness arc 34. In different time periods, a different number of food units may be expected. The "expected food units" during, e.g., a ten minute time frame can be used as the number of units that would maintain weight neutrality and the observed variance from expected food units could be used to determine the rate at which energy can be being transferred to i) fat which can be stored energy (i.e., weight gain), or ii) removed from energy stores and converted to heat plus kinetic energy (i.e., weight loss).

The food unit increase or decrease from "expected" can be expressed as a (+) or (−) percentage. This percentage can be used in the fitness arc 34. More particularly, a negative percent that shifts the fitness arc 34 to the left can indicate an expected weight gain, and a positive percentage that shifts the fitness arc 34 to the right an expected weight loss. The units in the fitness arc 34 can be based upon relative value units or units of percent change. The affects of the power equation 1 on the fitness arc 34, as noted, can be modified by the power equation 2, discussed in more detail below.

Power Equation 2

In power equation 2, power P' can be defined as the rate at which work can be performed. More particularly:

$$\text{Power } P' = \text{Force} * \text{Displacement} / \text{time}. \quad \text{Power equation 2:}$$

Where force can be the energy needed to move a pre-specified mass a pre-specified distance per unit time.

Force can thus be defined as the ability to move the weight of the individual user (i.e., mass) a pre-specified distance in a pre-specified time. The pre-specified distance can be that which the individual can be able to move in an allotted time. The allotted time, as is disclosed in greater detail below, can be that time allowed by the programming of an accelerometer located in the activity module 14 worn by the user, which can, e.g., be used to count each deflection of the accelerometer in a specified general direction as a separate event. This time, may be, e.g., measured in fractions of a second. The distance traveled can be seen to depend upon the ability of the user to move his/her weight a given distance, which can be fixed by the individual's current unique locomotion characteristics. He/she can only move so far in the time allotted no matter what his/her level of effort because after a brief first number of milliseconds of acceleration, a terminal velocity can be reached and limit the distance traveled. Thus the distance that the user's mass can travel during the period of measurement can be seen to be fixed across a wide range of physical activities, e.g., walking, trotting, jogging, sprinting, etc.

Human physical activity can be episodic and therefore have nonlinear acceleration. Because the time allotment between separate episodes of acceleration can be set in fractions of a second, the activity module 14 can be, e.g., capable of counting sequential and multiple events, even though the events may be occurring in rapid succession. This can have the effect of allowing the activity module 14 to count activity units over a wide range of physical activities, as noted above, or, e.g., swimming, jumping, weight lifting, etc. and doing so in such a way that each count (e.g., a stride, swimming stroke, weight lifting repetition, etc., can be used to represent a user prescribed and constant activity unit, i.e., value for energy use by the user. The pre-specified time allotment can be a specified unit of time over which the accelerometer can be used to count each motion as a separate event.

As noted above, each displacement (or each displacement in a preselected general direction, can be utilized to equal the activity count. Time can be extended over a period of exercise or over a longer period of time, such as one week, or separately calculated and summed over the longer period of time. Force can be the ability to move mass (the weight of the individual) a specified distance (measured in accelerometer counts) in the time specified. The time between acceleration events of the accelerometer can be calculated by the application 12 as separate events. Because the application 12 can define force utilized by the user as a constant and displacement can be measured in activity units as described above, the power variance can be measured as a comparison of the accelerometer deflections per week.

This can be averaged over shorter periods of time, and, e.g., calculated to an average for 10 minute intervals. However, the units of displacement (activity units) of the user mass, walking or swimming, as an example and/or weight being lifted, e.g., can be expected to occur in pre-specified intervals. Therefore expected activity can also be seen as varying according to the time of day. There can be, e.g., an expected number of activity units per unit time and an observed number. This relationship can be represented as a percentage change whereby an increase percentage of activity units can be utilized, e.g., to shift the fitness arc 34 to the left in region 34a, and a deficiency can be seen to shift the fitness arc 34 to the right to the region 34b. In addition, the entry of the activity unit percentage can also have a timed entry into the fitness arc 34 calculation regardless of what segment of the day in which they can be actually performed. This timing reflects the manner in which the total expenditure of energy to perform work W (wherein W=power×time) can be projected, e.g. in a physiologic model, rather than instantaneous in the physiologic model.

Overall, power equations 1 and 2 can each be given a relative weight and then summed to produce a percentage change in observed versus predicted food energy units consumed and activity unit energy expended. The depiction of this percentage change, taken together with the effects noted above as to indicated/predicted food intake, can result in the value shown on the fitness arc 34. The fitness arc 34 can thus represent absolute energy excess versus energy deficit or energy excess versus energy per unit time in specified units. The units can be defined in the power equation calculations, but where the fitness arc 34 can be expressed as a percentage change, the units need not be indicated to the user. Any units for the value shown on the fitness arc also would not provide any additional meaning because the fitness arc can be seen to be defined for each user and have value only in that the fitness arc represents a unit of comparison of energy balance for the particular user.

The application 12 can reference published calorie value(s) of a particular food being consumed by the user, but does not necessarily define the value inside the algorithm, particularly considering that the calculations within the algorithm can be based upon how the user represents the food intake and the impact of the represented food intake along with the represented activity level(s) impacts weight variance for the indicated food intake, when weighted against indicated physical activity, and considering the current value for intrinsic metabolism of the user. The published calorie content of food may be completely coincident with a food unit value, but the calculations of the algorithm used in the application 12 do not require any such equivalence for accuracy of its intended functions.

Calculated food units values can be independent of actual caloric intake used in the application 12 to describe the user's metabolism. The user can be enabled to know his or her metabolism's energy balance expressed as change in a fitness measure, e.g., an absolute and/or percentage change in weight over a given period of time, e.g., the loss or gain of one pound in one week. The display of this relationship on the fitness arc 34, on which, as noted, there can be no units, can be viewed as a degree of colored filling of one or the other of the two portions of the arc of the graph, i.e., 34a, 34b. The energy units can be derived from the power equation 1 which quantifies the rate of energy intake, which, to the extend such exceeds the intrinsic metabolism for the given user, and if not expended, can be transferred into stored energy (fat), which can be expended in the form of energy used in activity by the user, i.e., energy units taken in modified by the power equation 2, (i.e., the movement of the individuals mass over a specified distance per unit time).

Since movement requires that force be delivered over a specified distance in a specified time on a specified mass, an energy unit can be derived which can predictably modify the fitness arc 34 energy transfer representation in a manner which reflects an energy balance (at least a predicted energy balance) for the user, e.g., at 10 minute intervals. Therefore, the fitness arc 34 can be used as a representation of energy balance as quantified by the energy transformation of food into fat or food into physical activity per unit time, such as, the relative movement of the mass of the individual user over distance per unit time.

It should be understood that the calculation for weight gain can be mathematically the same as the weight loss calculation. The calculations can be weight neutral algorithms. For instance, in the weight gain algorithm, one pound can be added to the neutral or per unit time, e.g., weekly, base weight. In this way the application 12 can allow the user to gain one pound each week by eating calories in excess of the number needed for weight neutrality. The intra-week calculations can be utilized, e.g., to allow for appropriate calorie (food unit) intake to limit weight gain to the desired one pound per week, taking into account, as noted above, the energy expended or to be expended by the user in the week. More specifically, in the weight gain algorithm the user can be instructed to push the fitness arc 34 into the red or energy excess portion 34b of the fitness arc 34. If at the end of the given week, the user weight of the user can be more than the desired weight gain, the food unit allowance can then be readjusted downward, to provide less extra calories for achieving the desired weight gain of one pound in the next week.

Continuing to refer to FIG. 6, in an embodiment, located above the fitness arc 34 can be a series seven color coded dots 36. At the end of each day the fitness arc 34 can be used by the application 12 to assign a color to one or more (?) dots 36 representative of a given day of the week. The current date can be located in the bar above the dots 36, and the dot 36 corresponding to the current date can be indicated, e.g., by being underlined (not shown in FIG. 6). There can be one dot 36 for each day of the week. The series of seven color coded dots 36 can be utilized, e.g., to summarize the fitness arc 32 results for each of the seven days. The dots 36 may be green to indicate positive fitness gain for a given day, black for neutral, or red for weight gain. For a given day, the dot 36 can be green if the fitness arc 34 can be fully green, red if fitness arc 34 can be fully red, and black if the fitness arc 34 is not a full color. The accumulation of 7 green dots 36 can indicate that the expected one pound of weight loss should have occurred, and a mixture of color dots 36 can be seen to indicate a variable effect on weight and fitness. The occurrence of a red dot 36 can be seen to indicate a slower progress with the weight loss process. The energy intake excess, e.g., as indicated by the red dot 36 can indicate the undesirable effect of resetting the body of the user to a natural state which can be to store fat rather than break it down. Day to day variations, particularly of more than ½ of a pound, can be most likely fluid gain or loss. These variations can be difficult to interpret in isolation. The system 10 over time can calculate actual changes in body mass that, e.g., are not the result of water weight fluctuations.

Continuing to refer to FIG. 6, in an embodiment, a circular shaped activity circle 38 can be utilized to indicate the amount of physical activity (e.g., exercise or motion) achieved for a given day, or, alternatively, cumulatively over the given longer time period. The activity circle 38 can be filled using data provided from the activity module 14, e.g., wirelessly. The activity module 14, as noted above, can recognize different types of activity, such as aerobic, intense aerobic, weight training and intense weight training, as disclosed above and in further detail hereinbelow.

The activity circle 38 can represent the expected activity of a user, e.g., based upon the history of the amount and type of activity performed by the user. If the behavior of the user changes, the amount of activity needed to fill the activity circle 38 can be changed. No individual has the same level of activity from day to day. The application 12 can adjust the user's food allowance throughout the day based upon what activity can be expected and what has actually occurred. The activity circle 38 can fill up at different rates, for the same number of activity units, for different users. In other words, the rate for filling the activity circle 38 for any given exercise can be variable for each user and also can be partly or fully based on a learned activity pattern learned by the application 12, based upon the prior behavior of the user. In an embodiment, should the user conduct more activity than the application 12 historically expects, the activity circle 38 can display progressive series of colors indicating the amount of activity increase. Changes in the activity circle 38 can have an immediate impact on the fitness arc 34.

Any prediction made in determining the fitness arc 34 (i.e., the calculation of an energy deficit/energy excess) may be confirmed through the input of the user's daily (or other periodic entry) actual weight. If the prediction by the system 10 is incorrect, the system 10 can adapt to the user's circumstances. For example, if the user underestimates the indicated food intake portions, the user may gain weight, even though the fitness arc 34 indicates an amount on the energy deficit side 34a of the fitness arc 34. As disclosed above, the application 12 can recognize this and make adjustments that enhance the accuracy of the fitness arc 34 accordingly. Similarly, if the user does not burn calories as rapidly as initially predicted (and therefore an initial prediction by in the energy deficit portion 34a may result in an actual energy excess), the application 12 can recognize this and adjust the fitness arc 32 accordingly.

The units which describe activity and food choice can be specific to each user, and can be learned for each individual and adjusted daily. For example, they can be different from the conventional food caloric units, which can be used as measurement of physical activity, or the unit of energy liberated in heat generation from a specific food. The food calorie units can be entered into the application 12 initially, but the units change as they can be measured against other variables, and they can be assigned a unique user specific number within the algorithm. There can be constants assigned to the user, e.g., which represent intrinsic metabolism, but this number can be recalculated as food icon selections, activity and fitness affect the user's actual and changing level of intrinsic metabolism.

The application 12 can consider metabolism as the efficiency with which the user utilizes stored and consumed calories and therefore represents an element of the energy balance. Thus calories assigned to food or activity for example, can be different from those assigned from existing data bases, but instead can be defined by the way in which the user inputs data and the way the data as input interacts to establish the metabolic constant calculated by the application 12. The values assigned can be recalculated based upon their ability to accurately predict weight gain or loss. The fitness arc 34 can represent a real time presentation of the system 10 assessment of the energy balance. In an embodiment, the fitness arc 34 periodically updates (e.g., every 10 minutes) and displays the energy balance relationship between food, activity and metabolism. As described hereinabove, at the end of each day, the fitness arc 34 data can be assigned a final value which then can be represented by the green, red, or black dot 36. The ratio or proportion of the color coded dots 36 over, for example 7 days, can visually inform the user as to whether there can be an expected weight loss or gain during a particular week. The algorithm thus creates an ongoing user profile of intrinsic metabolism, activity, food choice and food amount that can be unique to each user.

Continuing to refer to FIG. 6, a colored diamond-shaped pointer 40 can be movable along a line that represents a range of a health quotient 42. The health quotient 42 can be derived from the running average of the fitness arc value 34c for each day of a month modified by the food type consumed and the user's weight. The health quotient 42 can include the user's present weight and desired or targeted weight (i.e., via direct input), the quantity and type of food consumed (i.e., based on the user's selection of food types and quantities). The health quotient 42 also can include the aerobic activity of the user (such as running) and anaerobic activity (such as resistance training for muscle enhancement) which can be automatically input into the application 12 by the activity module 14 as disclosed in more detail below.

In an embodiment, the heath quotient 42 can be a graphic representation of a single point on a horizontal scale of the health and fitness of the user as referenced against his/her goals and profile. The heath quotient 42 can be contrasted to the fitness arc 34, which can be a measure of daily energy balance, because it places the user on a scale of fitness and health based on data accumulated over longer periods, e.g., one month. The determination of health can be not culled or determined from a demographic reference point, but instead determined for each user based upon parameters defined in the application 12 (i.e., target weight, calculated intrinsic metabolism, food type and quantity consumed, the rate of change in weight gain or loss of the user, exercise and activity units level, etc.). The heath quotient 42 calculation can incorporate the directionality of measured values and inputs for the user to establish health status. The heath quotient 42 also can be given limitations as to its positioning on the scale based upon indicated weight goals. Specifically, the over weight individual (defined in the user profile input screen 24 by a targeted weight goal less than actual weight) could be restricted from a pointer 40 position on the fit zone of the heath quotient 42 horizontal scale. The location of the pointer 40 on the horizontal scale can also be determined by historic data from the user as well as daily updates which, when formatted by application 12, define the heath quotient 42. The horizontal scale can be a range of units for all users allowing for standardization and comparison among individuals and groups, but the data and profile for each user defines the degree of movement on the scale conferred by the various parameters of the algorithm(s) used in the application 12. In other words, the scale can be constant across all users, but the amount of change or movement on the scale per calculated value(s) of the application 12 parameters can be different for each user. Thus the user can set individual goals, but where the pointer 40 can be positioned on the health quotient 42 scale can be based upon the application 12 algorithms' calculation of the user's specific metabolic profile.

As disclosed above, the starting weight 24b and target weight 24d can be input on the user profile input screen 24 (see FIG. 3). Based on these inputs, one of two conditions can be possible: i) the user can be over weight (i.e., the starting weight can be greater then the target weight), or ii) the user can be at or under the target weight. These two possibilities can be used to govern the health quotient 42. More particularly, in an embodiment, when the health quotient 42 is calculated at the end of each day, the pointer 40 can be positioned in a manner described below.

The health quotient 42 horizontal scale can range, e.g., from −50 units at the left end to +50 units at the right end, although the numerical values for the units are not shown on the scale on FIG. 6. Each month, a running average of available health quotient 42 daily results can be compiled and displayed. When moving from one month to the next, the first day of each month can be equivalent to the final figure from the previous month, and it can be weighted as only one day of that month. As shown in FIG. 6, the horizontal scale can be divided into four portions moving left to right. The first portion extends from −50 to −25 and can be labeled "fit", the second portion extends from −25 to 0 and can be labeled "healthy", the third portion extends from 0 to +25 and can be labeled "unhealthy"; and the forth portion extends from +25 to +50 and can be labeled "health risk". In an embodiment, each portion may have color coding varying from "fit" to "health risk" such as dark green, green, yellow, and red, respectively. The position of the pointer 40 on the horizontal scale can be used to represent, at the end of each day, that month's average of health quotient 42 values over the available days in the month. Furthermore, the health quotient 42 units can be the fitness arc values 34c of the fitness arc 34 at the end of each day, e.g., as modified in a manner described below.

In an embodiment, the health quotient 42 may also account of the distribution of the calories consumed thought the day. More particularly, the waking hours are divided into four quadrants. If 20 percent of the total food consumption is consumed in each of the four quadrants, then the pointer 40 will shift to the left by three units, and if not, it will shift to the right by three units. The remaining 20 percent can be consumed in any of the four quadrants without effecting the health quotient 42.

In the circumstance where the user is over weight (i.e., the starting weight can be greater then the target weight), the pointer 40 can point to a point to the left of −24. The user could thus be in the "healthy" range but not in the "fit" range. Food selection can also modify the final number. Each food item can be assigned a color: for example red for poor quality, yellow for neutral quality, and green for high quality food. Further, when consumption of 51% of food is good quality or poor quality then the following modifiers can be activated, and if consumption of either the good or poor quality food does not reach 51%, then these modifiers may not be activated. The modifiers and their triggers can be:

If 51 percent of food consumption is "good quality" and the user is overweight then the final fitness arc 34 can have negative, e.g., 12 units added to fitness arc value 34c and the pointer 40 can be shifted to the left. If 51% of food consumption is poor quality, then the pointer 40 can be shifted to the right, e.g., by 12 units.

If the user is at or under target weight and 51% percent of food consumption is "good quality" then the pointer 40 can be shift, e.g., (50+12) or 62 points to the left. If 51% of food consumption is "poor quality", then, as described above, the pointer 40 can be shifted, e.g., to the right by 12 units.

The system 10 can also reference food intake with change in the user's weight and fitness activity to develop the user's intrinsic metabolism. As described above, the system 10 may adjust the prediction of changes in the health of the user on a daily basis based on input values from the user regarding weight, food intake and fitness activity.

In an embodiment, a summary of each month's health quotient 42 may be displayed (not shown). For example, the display may provide a listing such as: i) January—fit, ii) February—unhealthy, etc.

Figure 7A:
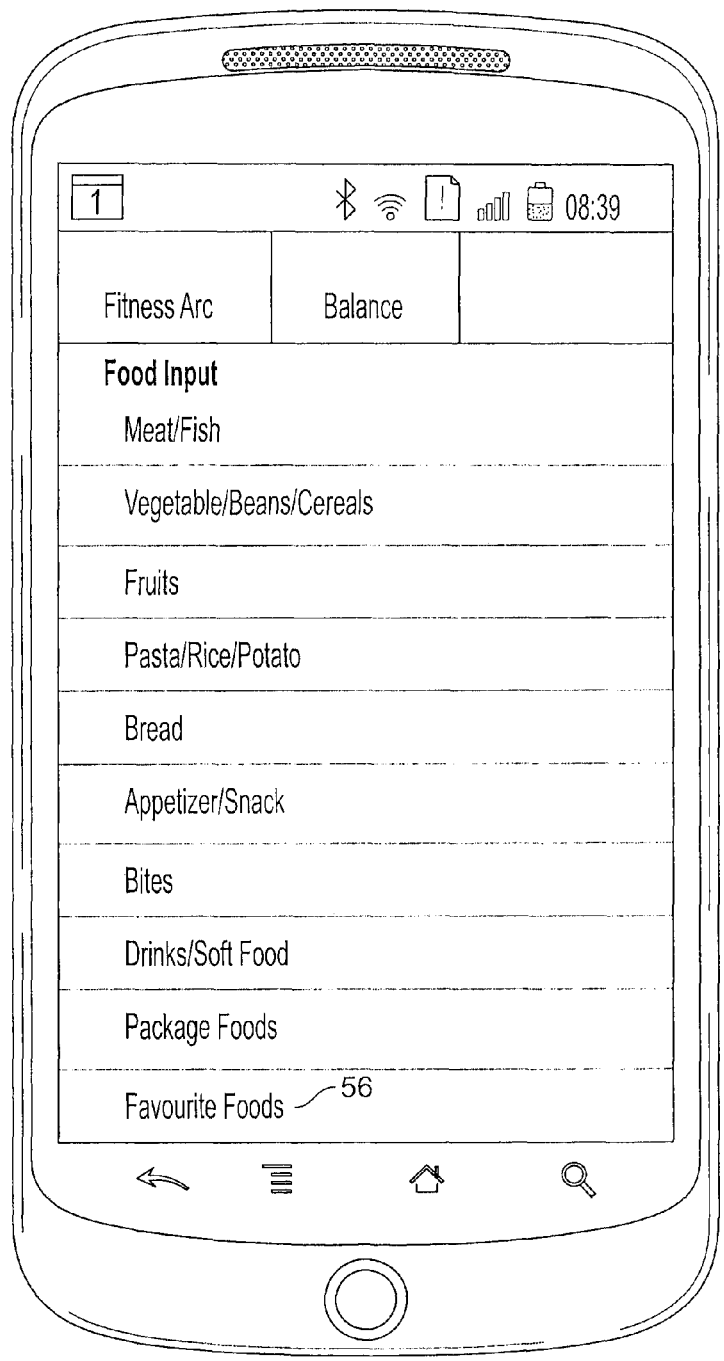
FIG. 7A shows a user food choice input screen.
Figure 7B:
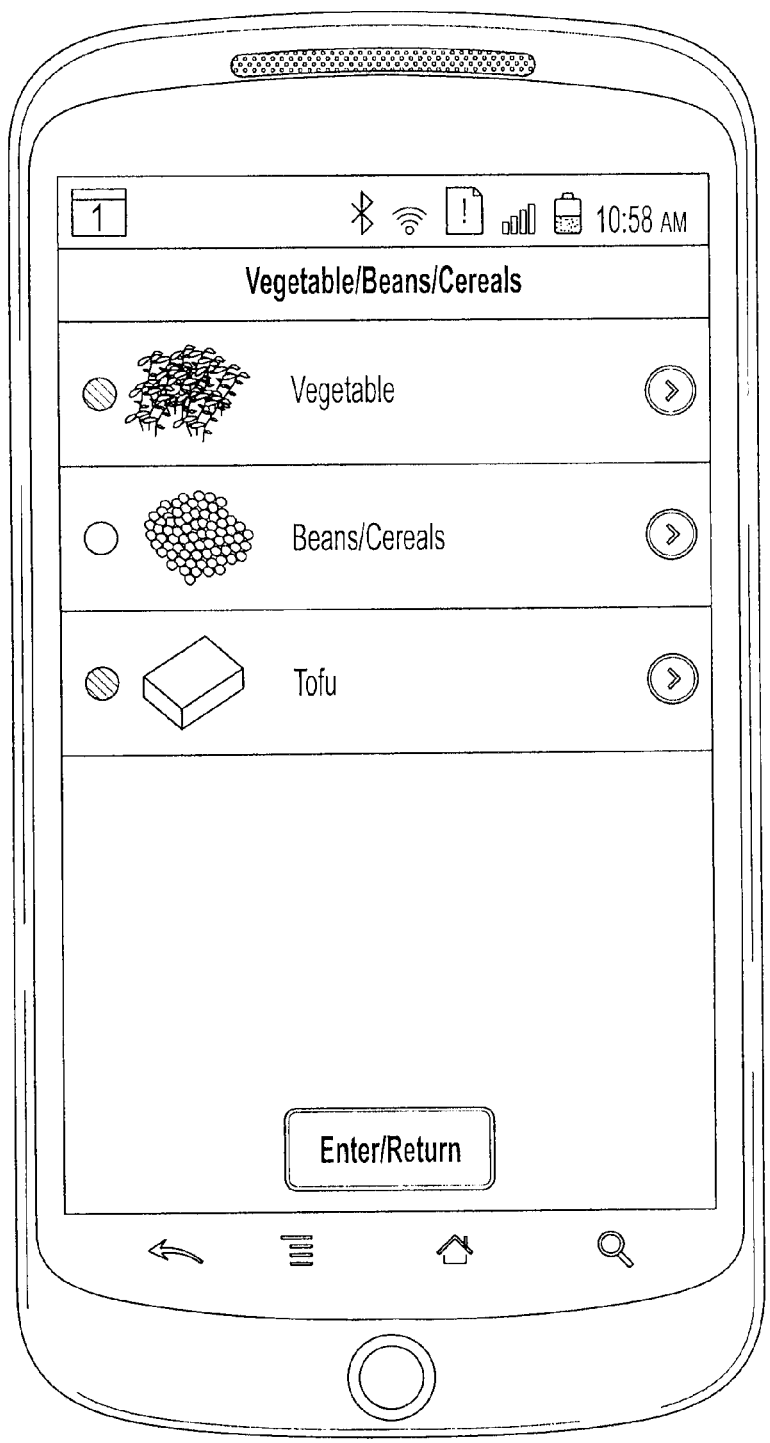
FIG. 7B shows an another user food choice input screen.
Figure 7C:
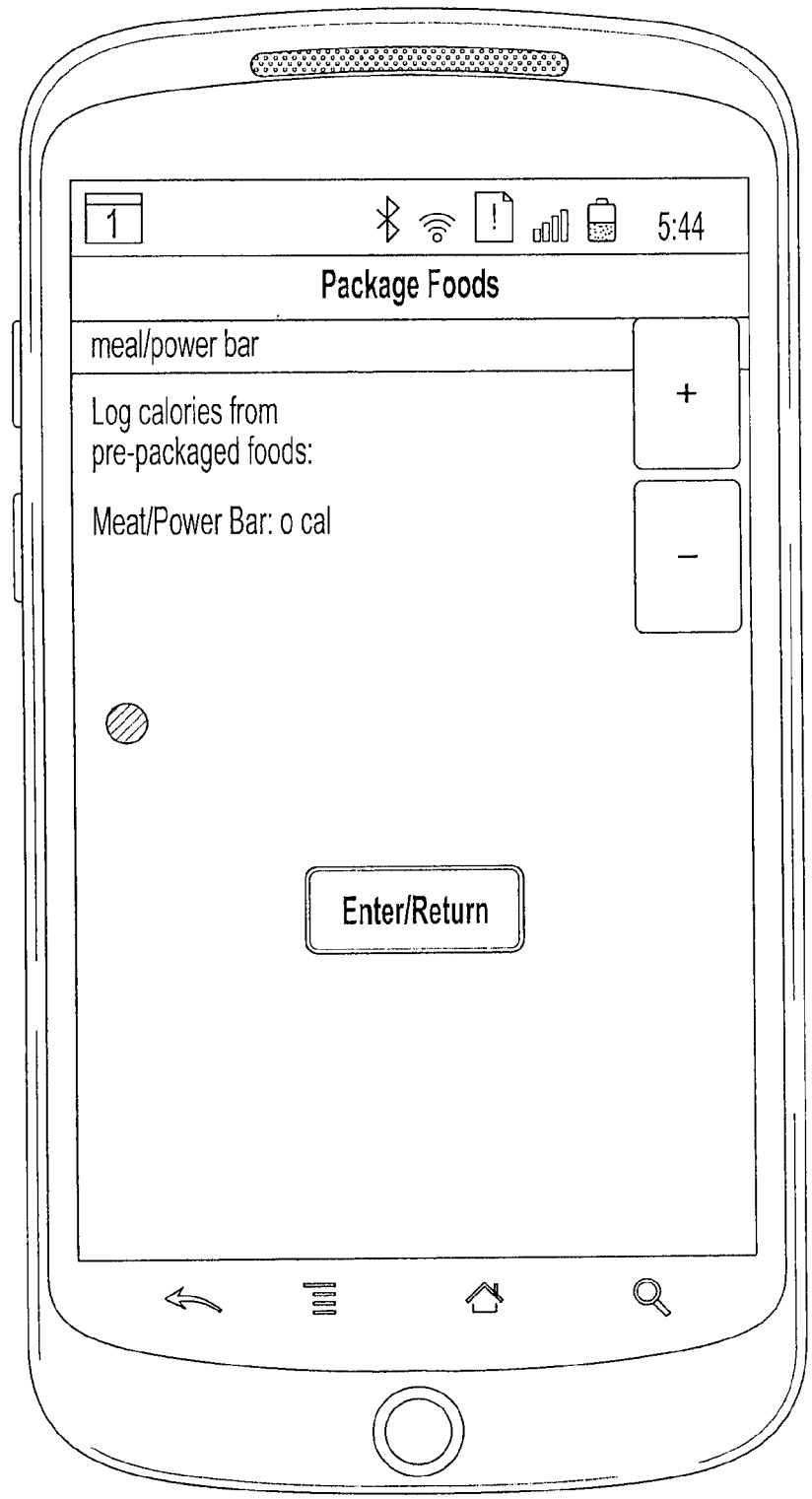
FIG. 7C shows an another user food choice input screen.

Referring now to FIGS. 7A-7C, as described above, when a user consumes foods, it may not be necessary for the user to directly input the number of calories. Instead, the user may select the type of food consumed from a listing 44 as shown in FIG. 7A and further defined in the listing shown on the screen as indicated by way of example in FIG. 7B. In an embodiment, the application 12 may learn the user's most frequently chosen or consumed food choices, and compile the same under a tab on the listing 44 (see FIG. 7A "favorite foods" tab 56). A dietician can review the listing 44 and repopulate it. When the user can read calories off a food package, the item may be entered directly on the screen depicted in FIG. 7C. In such instances, the food percentage of protein, fat, etc. components may be provided by the application 12 for such items, based on the normal distribution of these components for such items. In an embodiment, the listing 44 may include items such as deserts and junk food (not shown).

Figure 8:
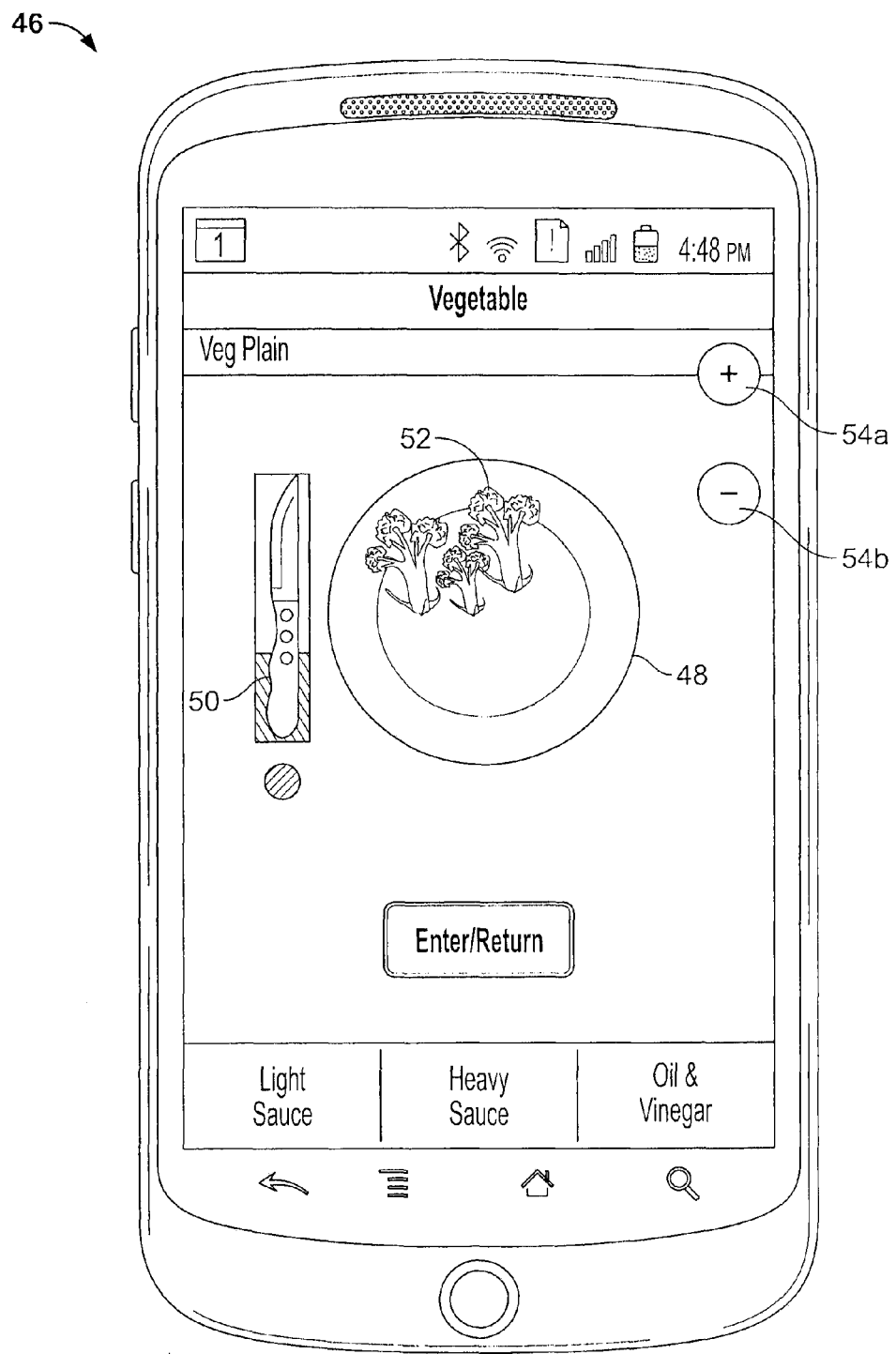
FIG. 8 is a user food portion input screen.

Referring to FIG. 8, in an embodiment, once a type of food is selected, a portion screen 46, including a plate 48, can be displayed. FIG. 8 also depicts a knife 50, or some other utensil for a size reference. The user may place more or less food 52 on the plate 48, e.g., with portion control buttons 54a, 54b. In an embodiment, the knife 50 can fill with a color scheme which depends on the portion size of the food 52, where the degree of coloring of the knife 50 equates with the degree of filling of the food circle 20 (FIG. 2) allowance. This can allow the user to visually input the type and portion of food, without the need of measuring, weighing or knowing the caloric content of the food. In an embodiment, the listing 44 may include an option for the user to input (e.g., download) a new food item(s) on the listing 44. The user may also manually directly input a caloric intake item.

In an embodiment, the user may enter a "proposed" meal to determine the meal's effect on the user's fitness goals. The user may then edit the proposed meal or change the proposed meal into an actual meal, e.g., after the meal is consumed. In an embodiment, the impact of the proposed meal on the user's food and caloric balance can be demonstrated by the knife 50 progressively filling with a color scheme which matches the color scheme and the degree of filling of the plate 48. Thus before the user enters the content of the meal into the application 12, the effect of the proposed meal can be seen by reviewing how much color the knife 50 has filed in. Reducing a food portion size can decrease the percentage of the knife 50 coloring. A fully colored knife 50 can be used to correspond to a fully colored food circle 20.

Figure 9:
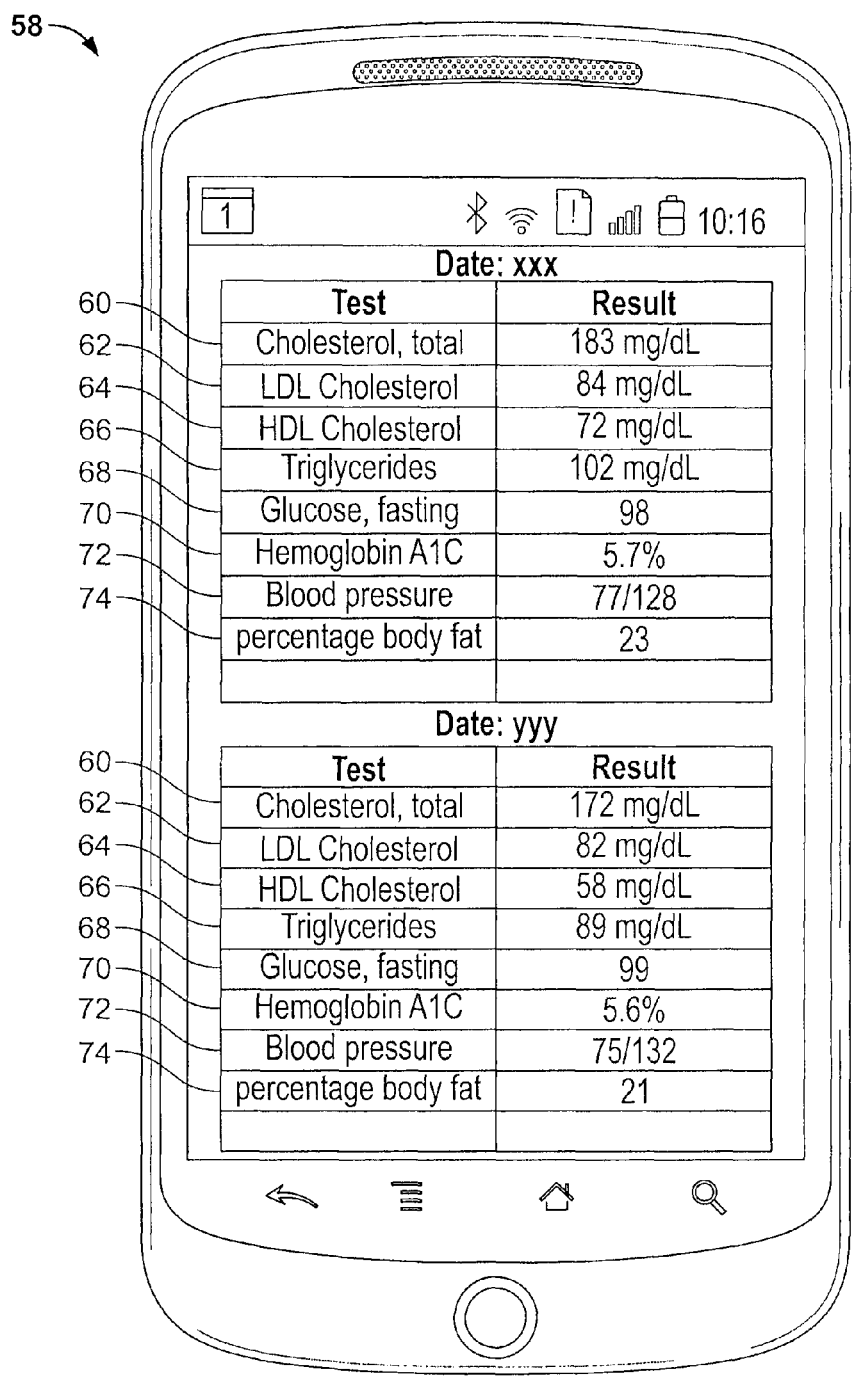
FIG. 9 is a user test results input screen.
Figure 10:
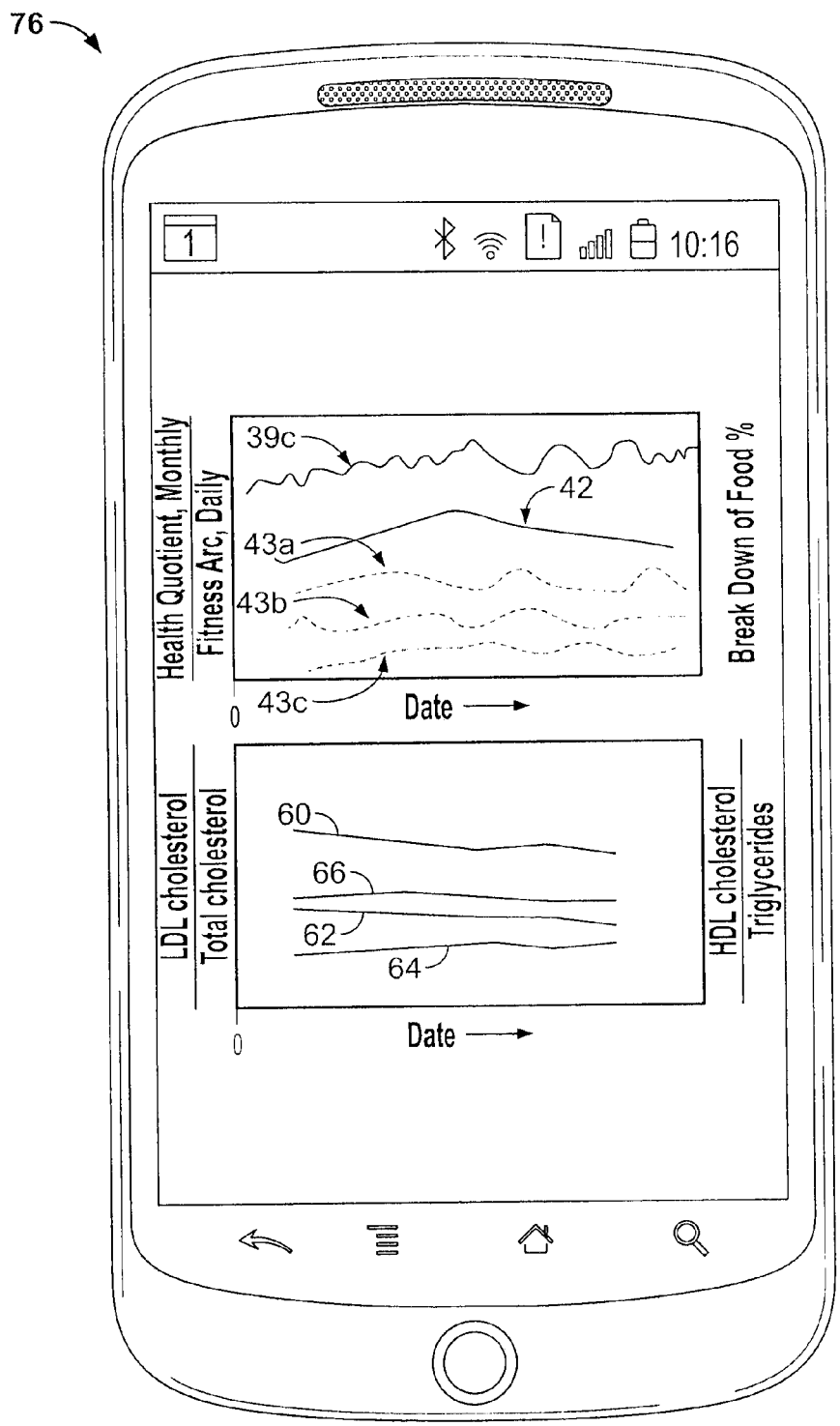
FIG. 10 is a screen showing a graph of user test results over time.

In an embodiment, in addition to accumulating and displaying fitness and heath related data generated by the application 12, the system 10 can facilitate accumulating and displaying externally generated fitness and heath related test results, thereby serving as a focal point for accumulating, storing and displaying all fitness and health data related to the user, not just the data provided by system 10. For example, test results may be periodically input in the application 12 by the user on a test results record screen 58 shown in FIG. 9. In an embodiment, FIG. 9 includes data on total cholesterol 60, LDL cholesterol 62, HDL cholesterol 64, triglycerides 66, fasting glucose, 68, hemoglobin A1C 70, blood pressure 72, and percentage body fat 74. It can be understood that other test results data may also be included in the test results records 58. The application 12 can then utilize the test results record screen 58 data to form historical graphs or histograms. For example, FIG. 10 depicts a graph or histogram 76, which shows total cholesterol 60, LDL cholesterol 62, HDL cholesterol 64, and triglycerides 66 blood test results for the user taken at various dates. Further, since energy excesses 34b may raise cholesterol levels, energy excesses 34b may be calculated and displayed (not shown) on the histogram page 76.

Figure 11:
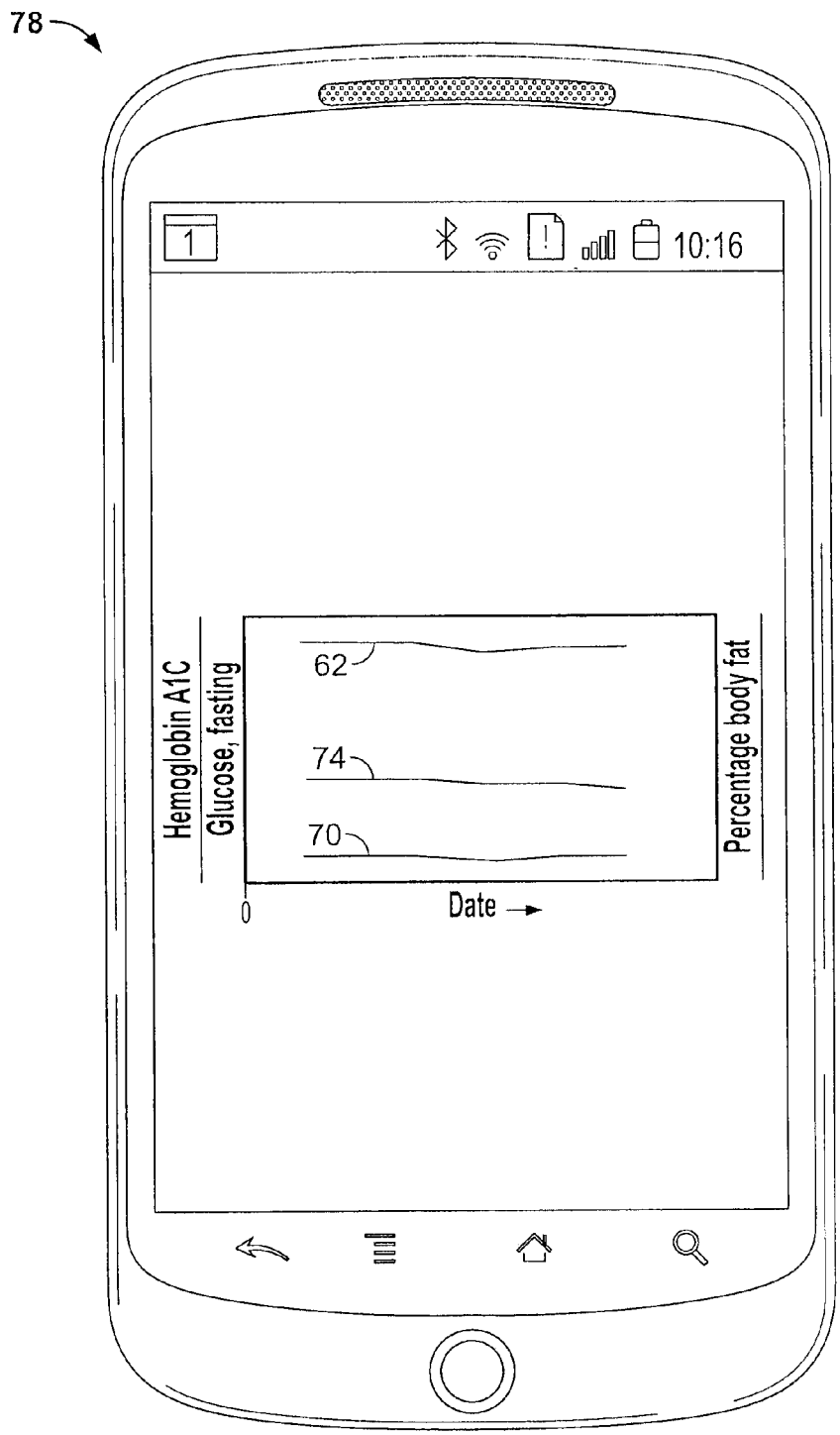
FIG. 11 is a screen showing another graph of user test results over time.

Referring to FIG. 10, in an embodiment, the system 10 can generate parameters such as the fitness arc value 34c, the health quotient 42, and the breakdown of food percentage 43a, 43b, 43c, etc., which may also be displayed in the histogram 76, to show correlations between the system 10 derived parameters and the externally derived test results (e.g., total cholesterol 60, LDL cholesterol 62, HDL cholesterol 64, and triglycerides 66). In an embodiment, FIG. 11 there is illustrated, by way of example, a histogram 78 for displaying test result measurements such as fasting glucose 68, hemoglobin A1C 70, and percentage body fat 74 over time. The system 10 may also generate other histograms (not shown) for displaying, e.g., the percentages of protein, fat, and carbohydrates, so that the food choice percentages utilized by the user and their trends over time can be also readily apparent to the user.

In an embodiment, the system 10 can facilitate accumulating and displaying data that can be related to health conditions that are being medically treated by the user. For example, Coumadin is a blood thinner prescribed to patients with a propensity to form blood clots in the vascular space. Such patients must monitor their intake of vitamin K (Vit K), which diminishes the effectiveness of the blood thinner. Vit K is known to occur in certain foods such as vegetables. The diet for patients on Coumadin therapy may be not focused on Vit K avoidance, but rather it can be based on the consumption of the same amount of Vit K each day.

Figure 12:
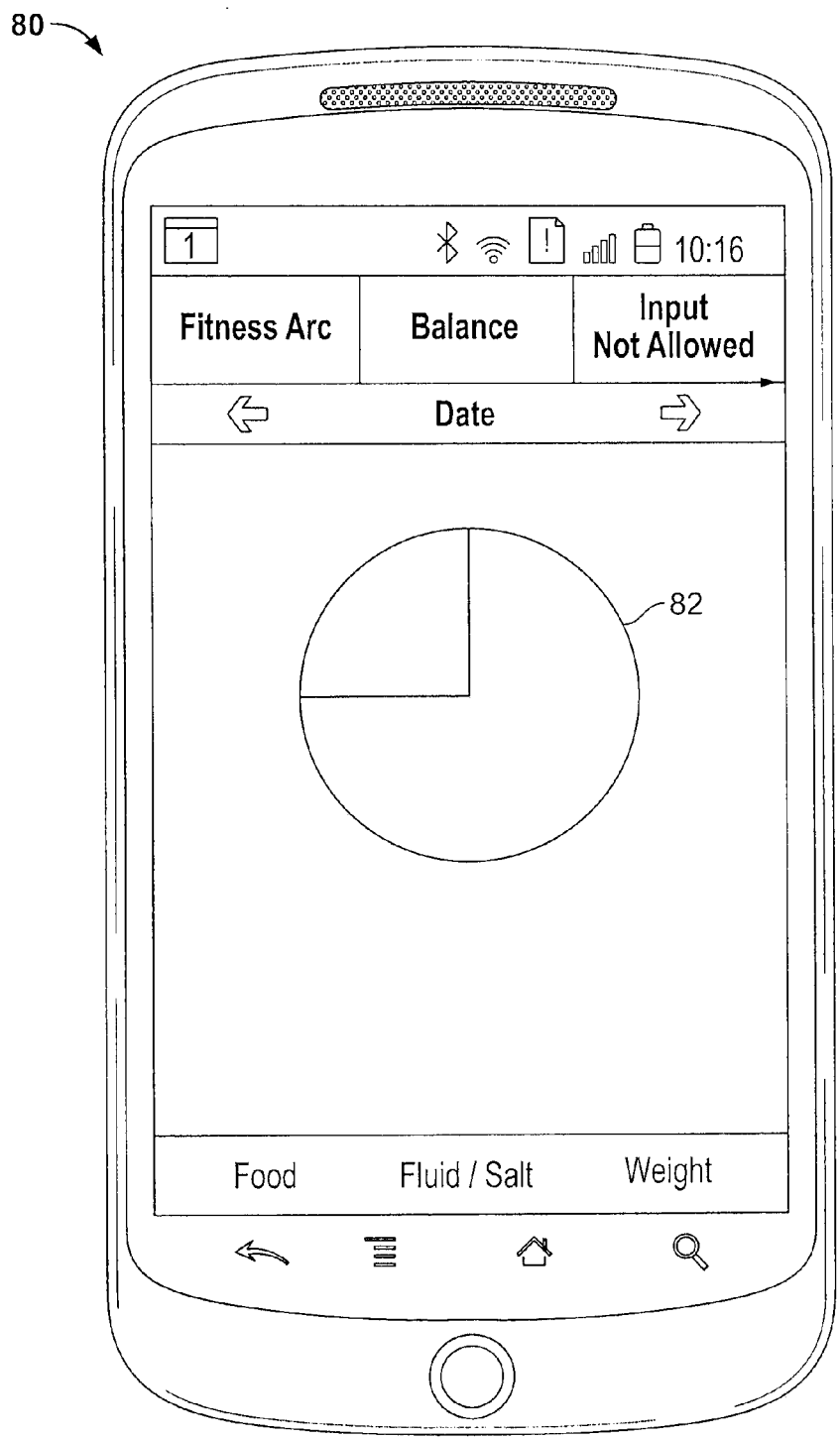
FIG. 12 is a screen showing a graphical circle that indicates the proportion of Vitamin K daily allotment consumed by the user during the day.

Referring to FIG. 12, Vitamin K chart 80 includes a Vit K circle 82 which can provide a graphical representation of the user's daily consumption of Vit K. If the diet of the user fills the Vit K circle 82 the same amount each day, then the effectiveness of the Coumadin therapy can be maintained. The Vit K circle 82 functions in much the same manner as the activity circle 38, and it can be learned for each user. The application 12 can learn and then stores a weekly average value of Vit K units which serves as a record of the user's Vit K units consumption behavior. The Vit K circle 82 may fill with green color as the units are accumulated toward the weekly average. More particularly, a numerical value of 1, 2, or 3 Vit K units can be assigned to each vegetable in order to describe its Vitamin K level. For example, if the user ate 100 calories of food assigned the numerical value of 1 Vit K unit, the application 12 could register 100 Vit K units on Vit K circle 82. If the user consumed 100 calories of food assigned the numerical value of 2 Vit K units, then 200 Vit K units could be registered on the Vit K circle 82.

The user can choose, on the profile input screen 24, whether to display a circle depicting whether the food consumed includes the total daily vitamin requirement or Vit K alone. The Vit K circle 82 may also fill with a green color (denoting a full daily allotment of Vit K has been reached), a yellow color (denoting a full daily allotment of Vit K I is being approached), or a red color (denoting a full daily allotment of Vit K I has been exceeded). In an embodiment, the Vit K circle 82 may alternately be displayed adjacent to the fluid and salt circles 26, 28 on FIG. 4 (not shown in FIG. 4).

Figure 13:
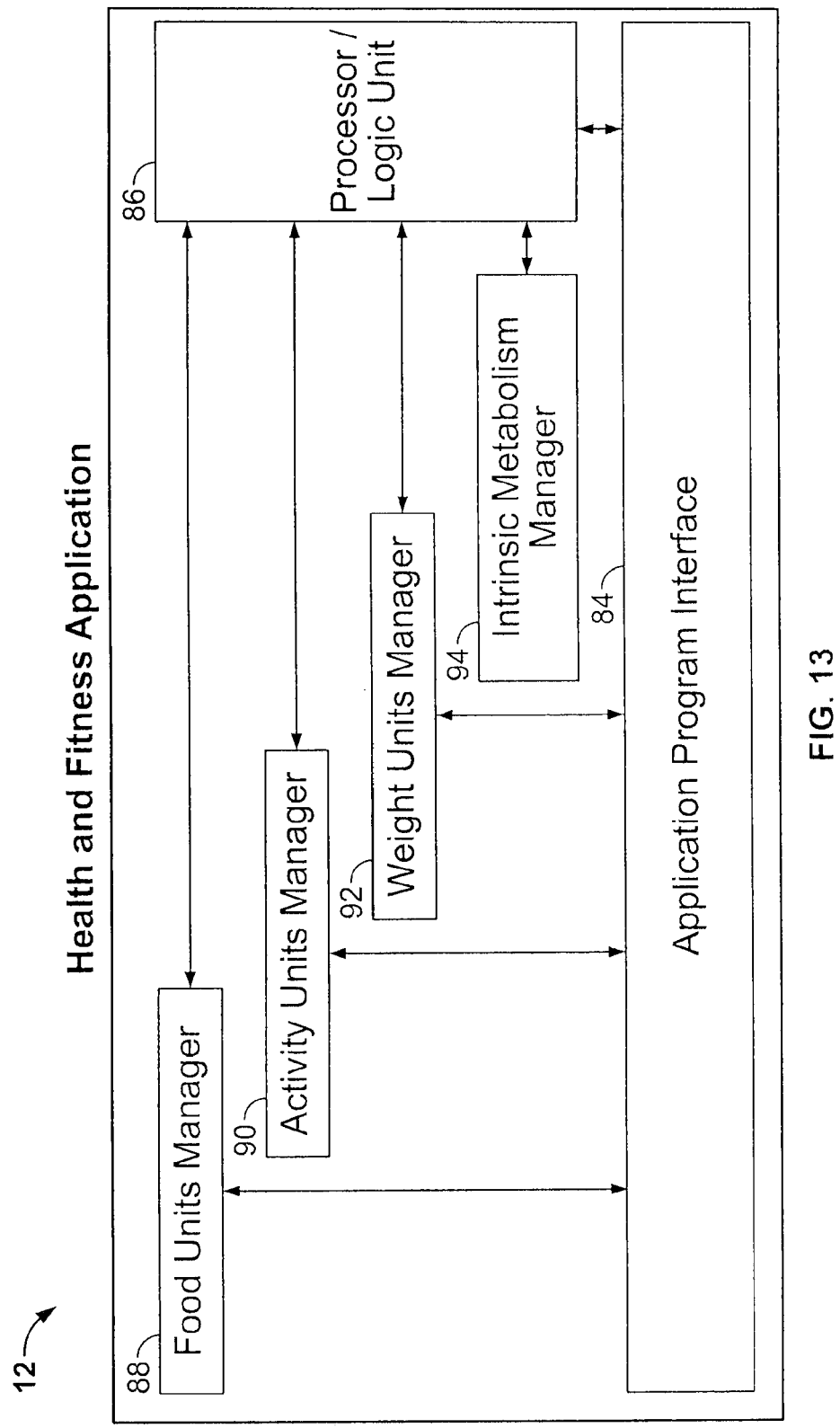
FIG. 13 is a schematic diagram of the health and fitness application.

Referring now to FIG. 13, as described above, the application 12 can include software algorithm codes for displaying data, calculating data, receiving data etc. In an embodiment, the application 12 can include an application algorithm interface 84 which can facilitate the interactions between the digital device D and the application 12 in a predetermined (e.g., standardized) manner. For example, the application algorithm interface 84 can enable the application 12 to utilize the conventional services and functions of the digital device D, such as i) the central processing unit, ii) the input/output interfaces (e.g., touch screen, keyboard, mouse, etc.), and iii) the Bluetooth™ transceiver. In this way, the software algorithm codes of the application 12 may employ these services to receive data, display data, and calculate using the data, etc. In an embodiment, the application 12 can be functionally organized around a processor/logic unit (computing device)

86 that can be connected to a food units manager 88, an activity units manager 90, a weight units manager 92, an intrinsic metabolism manager 94, and the application algorithm interface 84.

In an embodiment, the food units manager 88 and the weight units manager 92 can be interacted with the user via the user interface of the digital device D, and the activity units manager 90 can interact, e.g., wirelessly, with the activity module 14, e.g., via the Bluetooth™ channels BT1 and BT2. The results of the food units manager 88, the activity units manager 90, and the weight units manager 92 interactions can be input to the processor/logic unit 86 wherein the application 12 can periodically run the energy balance calculation and formulate the intrinsic metabolism and provides the same to the intrinsic metabolism manager 94. In the manner described above, the intrinsic metabolism manager 94 can assess the accuracy of the processor/logic unit 86 formulated predicted weight to that of the inputted actual weight of the user. Should the formulated/predicted weight be significantly different than the actual weight of the user, the intrinsic metabolism manager 94 can, e.g., direct the processor/logic unit 86 to formulate an adjustment, e.g., to coefficients provided to the food units manager 90 for adjusting the food unit values or to the activity units manager 90 for adjusting activity units as is further discussed below.

Figure 14A:
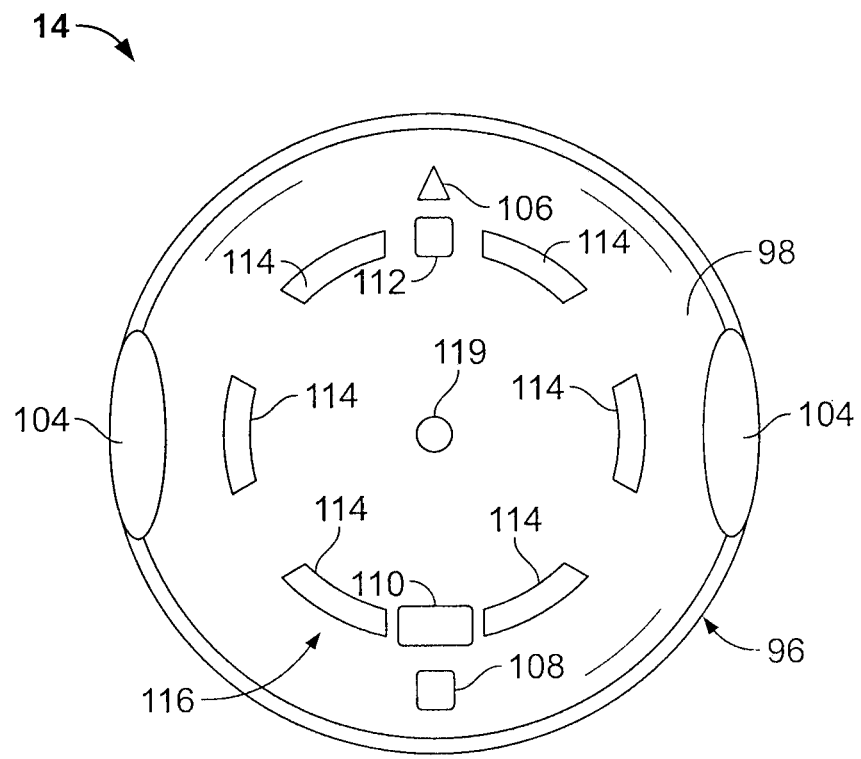
FIG. 14A is a plan view of the activity module.
Figure 14B:
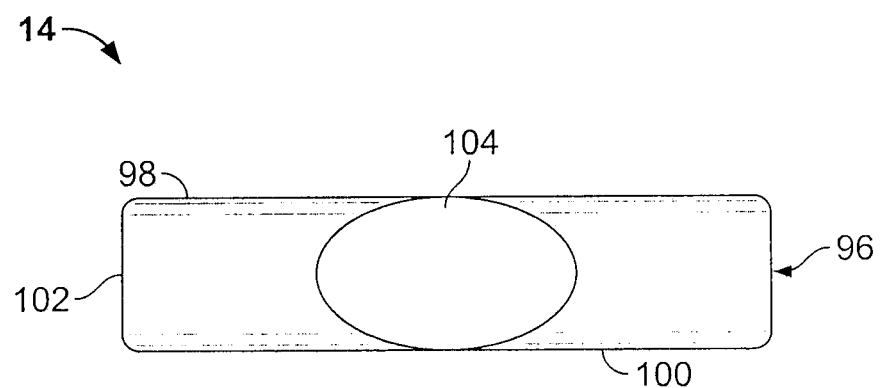
FIG. 14B is an side view of the activity module.

FIGS. 14A and 14B depict the activity module 14 which, when it can be worn by the user, can produce and stores activity units that can be conveyed, e.g., wirelessly, to the application 12. More particularly, the activity module 14 can be contained in a disc-shape housing 96 which can have a face 98, a bottom 100 which can be positioned opposite the face 98, and a cylindrical-shaped side 102 which extends between the face 98 and the bottom 100. In an embodiment, the bottom 100 may be releasably attached to the side 102 (e.g., threaded or clipped thereto) to facilitate the fabrication of the module 14 as well as, e.g., the replacement or recharging of batteries. The housing 96 may be made of plastic or other suitable material such as stainless steel. The activity module 14 may have a Bluetooth™ connection to application 12 of the system 10.

In an embodiment, the housing 96 can a plurality of indicators and buttons. More particularly, two buttons 104 can be positioned opposite each other on the side 102 of the housing 96. The user may turn the activity module on and off, e.g., by simultaneously pressing the buttons 104 with the thumb and forefinger and briefly shaking the activity module 14. The activity module 14 can shut down when it comes to rest for a selected period of time and can turn on when it senses motion. In an embodiment, both buttons 104 must be pressed simultaneously for all operations that require input from the buttons 104. An arrow-shaped pointer 106 can be located on the face 98 of the housing 96, for purposes disclosed below.

In an embodiment, the activity module 14 has magnets 108, 112 and an indicator light 110 that can be illuminated to indicate a low battery charge. The arrow shaped pointer 106 may also signal that the activity module 14 has the proper orientation in an exercise band 118 (FIGS. 15A, 15B), e.g., to record an aerobic exercise monitoring mode or a weight training exercise monitoring mode, which can be disclosed below.

In an embodiment, the activity module 14 can have a plurality of activity lights 114 which can be positioned on the face 98 of the housing 96, e.g., in a circular pattern to form an activity circle 116. The activity lights 114 e.g., can be progressively lit up during the day to indicate the user's progress in achieving his/her daily goal for activity units. A blinking activity light 114 can indicate that the activity units goal attributed to that particular activity light 114 has not yet been achieved, and a steadily illuminated activity light 114 can indicate that the activity units goal associated with the activity light 114 has been achieved. The activity circle 116 goal can be the number of activity units that can be required to be achieved by the user in the day to maintain his/her weight, or to be exceeded to lose weight, or to be under-achieved to gain weight and each of the activity unlit lights 114 in the activity circle can represent a percentage, e.g., 25% of this amount. In other words, the activity circle 116 activity units' goal can be also equal to the sum of each of the activity light's 114 activity units goal.

Assuming that the food intake is in a specified range, should the activity unit exceed expected levels, the daily food allowance can be increased as represented in the food circle 20 (FIG. 2). The object for the user can be to light up all the activity lights 114 during the day. The activity units circle 116 goal can be the same as that which can be applied to the activity circle 38 depicted in FIG. 6. The activity circle 116 goal, which can be calculated by the application 12, can be transmitted to the activity module 14 from the digital device D via the channel BT2. The number of activity units accomplished by the user at any given time in the day may be transmitted from the activity module 14 to the digital device D via the channel BT1. The activity module 14 can update its activity circle 116 independently from the application 12, once the activity module 14 has been informed by the digital device D how many units are required to illuminate all of the activity lights 114 of the activity circle 116. The transfer of activity units' data can be accomplished during a synchronization process which is discussed below.

In an embodiment, the user can synchronize the activity module 14 with the application 12, e.g., by pressing and holding the buttons 104 and double shaking the activity module 14. The activity module 14 can be then positioned within five feet of the digital device D, and the Sync tab located below the fitness arc 34 (see FIG. 6) can be then pressed. During the synchronization process, i) the activity units goal that has been calculated by the application 12 can be transmitted to the activity module 14 from the digital device D via channel BT2, and ii) the activity circle 38 of the application 12 can fill with accumulated activity units that can be transmitted to the digital device D by the activity module 14 via channel BT1. The user may synchronize the activity module 14 with the application 12 as many times as desired throughout the day, but preferably at least once a day.

Figure 15A:
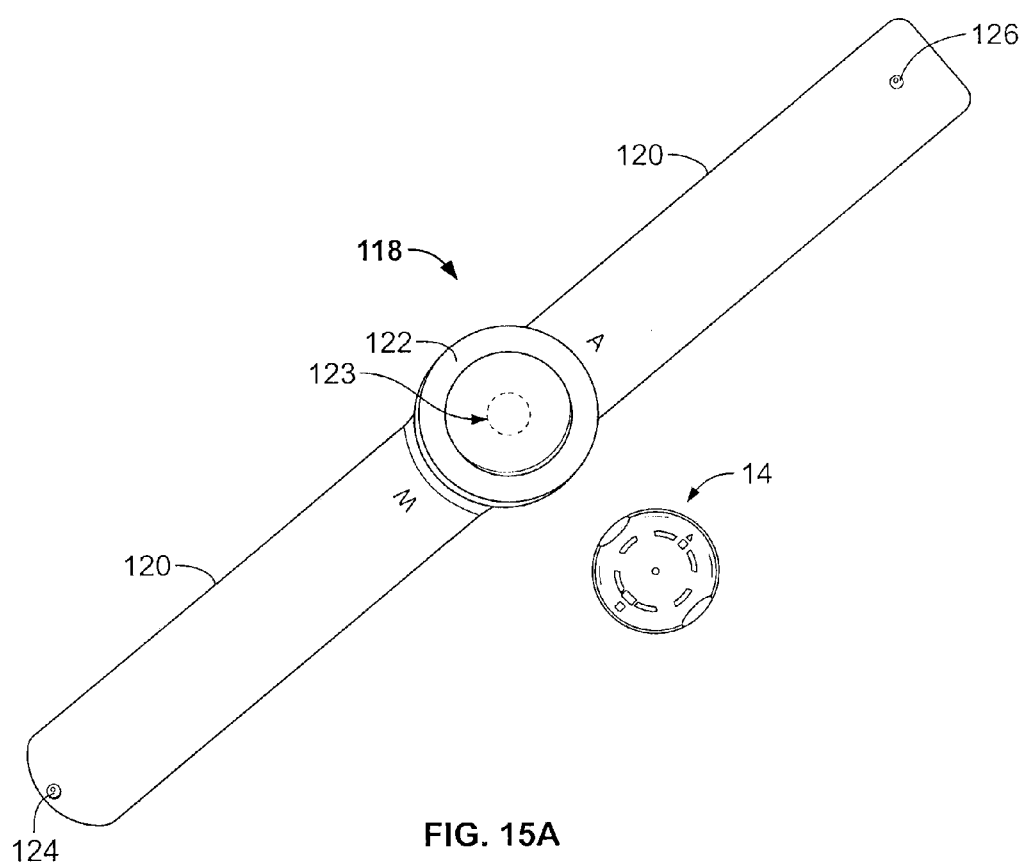
FIG. 15A is a plan view of a band which has a strap with a receptacle position thereon, the band can be shown positioned adjacent to the activity module.

FIG. 15A illustrates a band 118 that is depicted positioned adjacent to the activity module 14. In an embodiment, the band 118 has a strap 120 with a pouch or receptacle 122 that can be centrally positioned thereon. A magnet 123 can be embedded in the center of the receptacle 122, for magnetically retaining the activity module 14 in the receptacle 122. The strap 120 can have connectors 124, 126 that facilitate the releasable fastening of the strap 120 around the wrist or ankle of the user. More particularly, a pin 124 may fasten on one of a plurality of circular-shaped pin-catches 126. Alternatively, the connectors 124, 126 may be hook-and-loop fasteners such as Velcro®. The band 118 can be fabricated from an elastomeric material, such as rubber. Also, the band 118 may be formed as a bracelet, e.g., with a series of metal links that can be fastened about the wrist or ankle of the user.

In an embodiment, the strap 120 can be imprinted with an indicia A that can be located proximate to one side of the receptacle 122. The indicia A can represent a user aerobic exercise mode. The strap 120 can be also imprinted with an indicia W that can be located proximate to the opposite side of the receptacle 122. The indicia W can represent a user weight training exercise mode. Imbedded in the strap 120, located proximate to the indicia A, can be a permanent magnet (not shown) which can have one of its magnetic poles directed toward the receptacle 122. Imbedded in the strap 120, located proximate to the indicia W can be a permanent magnet (not shown) which has an opposite magnetic pole directed toward the receptacle 122. Alternately, the activity module 14 may be worn on a garment clip, in a pocket, on a lanyard, etc.

Figure 15B:
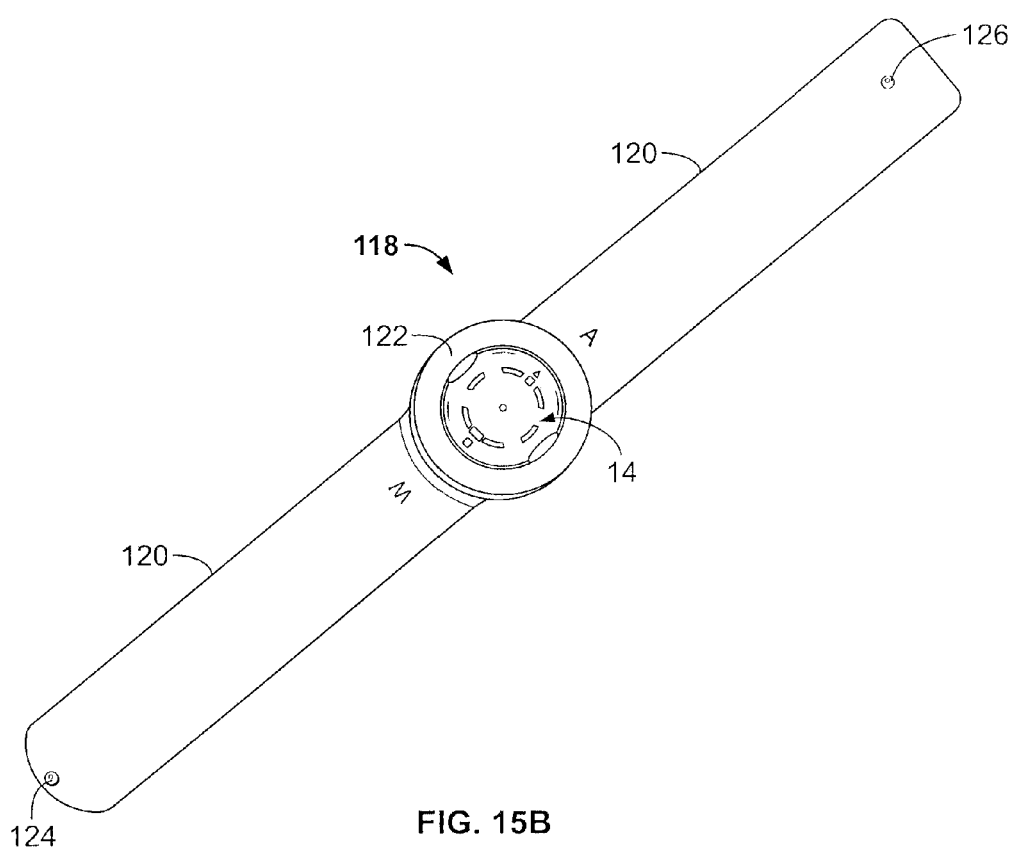
FIG. 15B is a plan view of the band shown in FIG. 15A in which the activity module can be shown installed in the receptacle.

Referring to FIG. 15B, the activity module 14 is shown installed in the receptacle 122. The receptacle 122 can be sized and shaped for removeably receiving the activity module 14, and due to the supple nature of the elastomeric material construction of the receptacle 122, the activity module 14 may be installed in the receptacle 122 by way of the user positioning one edge of the activity module 14 in the opening of the receptacle 122 and pressing the opposite edge until it can be fully installed in the receptacle 122. The activity module 14 may be removed from the receptacle 122 by pressing the exterior of the bottom of the receptacle 122, towards the bottom 100 of the activity module 14, until the activity module 14 is pressed out of the receptacle 122. This may serve to hold the activity module 14 within the receptacle 122 even without the magnet 123. In an embodiment, due to the supple nature of the receptacle, the activity unit 14 may remain installed in the receptacle 122 when the user simultaneously presses the buttons 104.

Figure 16:
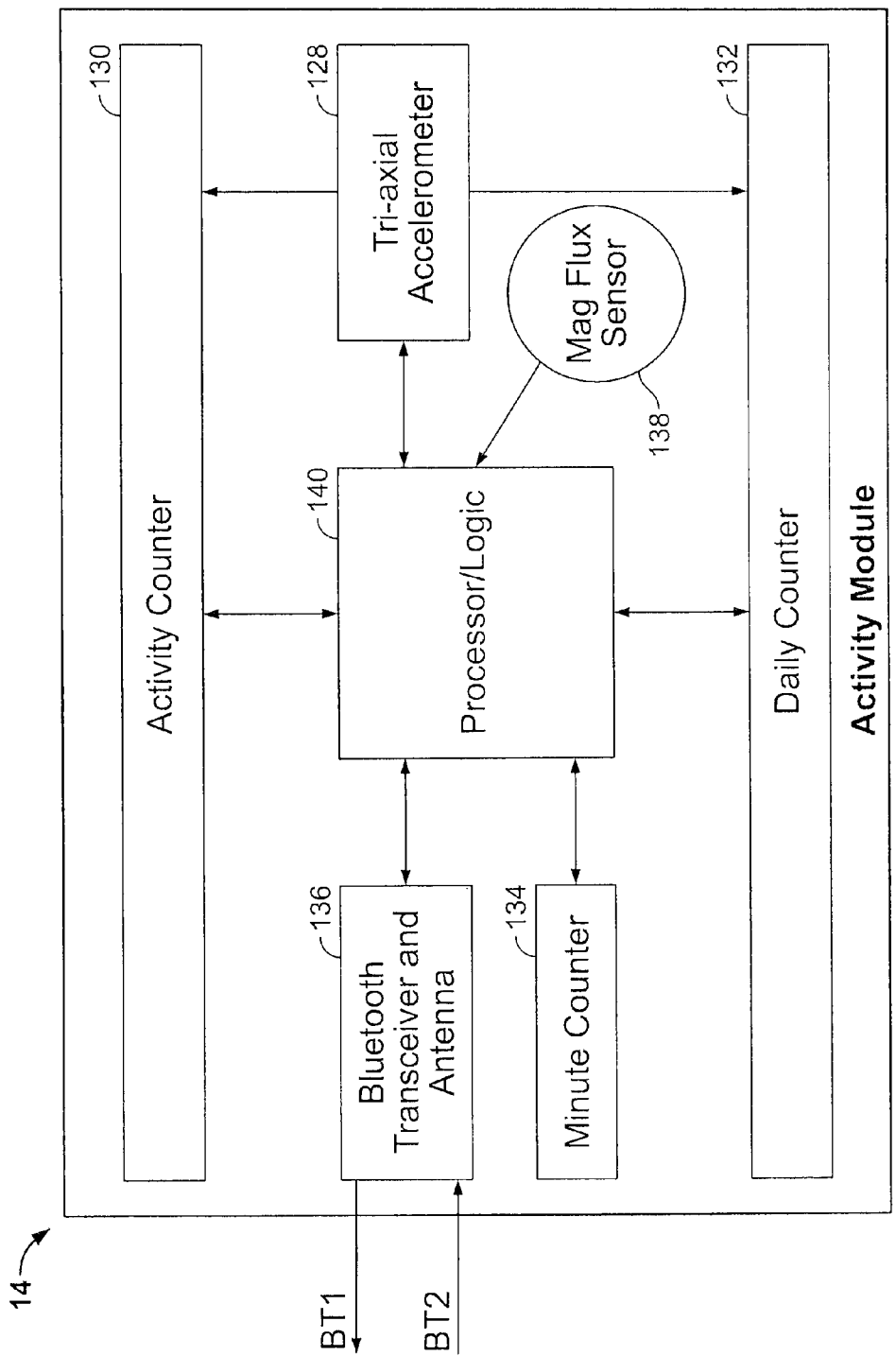
FIG. 16 is a schematic drawing of the activity module.

Referring to FIG. 16, the activity module 14 can include at least one multi-axis accelerometer 128, or alternatively two or three single axis accelerometers, an activity units counter 130, a daily counter 132, a time counter 134, e.g., a minutes counter 134, a Bluetooth™ transceiver 136, a magnetic flux field sensor 138, and a processor/logic (computing device) unit 140. The multi-axis accelerometer 128 can be a tri-axis accelerometer unit 128 that measures, e.g., the deflections of a suspended mass (not illustrated) in three orthogonal directions as a result of movement of the activity module 14. For example, any change in the movement of activity module 14 that is caused by changes in the movement of the user can cause an acceleration of the suspended mass in the X, Y and/or Z axis of the accelerometer 128, resulting in a deflection or "click" of the accelerometer 128 in X, Y or Z axis. Each such deflection can be used to produce one click, which can be equated to an activity unit or a portion of an activity unit, by the processor/logic unit 140 of the activity module 14, or alternatively, in some modes, two "clicks", one forward and one back, can be equated to an activity unit or a portion of an activity unit, in a manner discussed below. The activity units can be recorded and accumulated in the activity counter 130 and/or the daily counter 132, and can be transmitted (i.e., downloaded) to the application 12, e.g., by the Bluetooth™ transceiver 136, periodically and/or during the synchronization process that is described above. The activity units can be processed by the power equation 2, as described above.

The activity counter 130 can keep a running total of the activity units, e.g., until it receives a command from the digital device D. This data can be maintained for additional analysis, e.g., in the event that the user fails to download activity from the daily counter 132 which, e.g., may be configured to reset to zero every 24 hours, or to separately store daily accumulations for several days. The activity counter 130 can also start to count until it reaches the maximum value allowed by the hardware. At that time, it can be reset to zero. It can be, therefore, possible that the activity counter 130 may keep counting on multiple days. It will be understood that the user may command the application 12 to reset the activity counter 130 to zero by using a "clear activity" command (not shown) during synchronization between the digital device D and the activity module 14.

The daily counter 132 can maintain a running total of activity units for a 24 hours period(s). With each synchronization the application 12 can then calculate the difference between the last and current activity count for a given 24 hour period in order to update calculations and page displays. For example, the application 12 can update the activity circle 38 count and the expected number of activity units on the activity module 14. Therefore, the daily counter 132 can start to count activity units until the end of the day (i.e., when the minute timer 134 reaches a value of 1440 minutes) at which time it can be reset to zero. It will be understood that the application 12 can remember the daily counter's 132 value at the last synchronization so that the application can calculate the difference in the recorded values between synchronizations.

Since it can be possible that the activity unit 14 might not be in sync with the current time (at the minute level) during synchronization, the digital device D can set the minute timer 134 to the current time based on the digital device's D clock. This can assure that the application 12 and the activity module 14 both conclude a 24 hour (i.e., 1440 minute) period at the same time and can allow the user to travel to different time zones and maintain accurate application 12 functionality. At the end of the daily 1440 minute countdown, the activity module 14 can reset and begin a new count which can correspond to the next day.

The user can adjust the activity module 14 to measure an aerobic mode of exercise, or an anaerobic, e.g., weigh training, mode of exercise. This can be accomplished by orienting the activity module 14 in the receptacle 122 of the band 118 so that when the arrow-shaped pointer 106 is pointing to the indicia A, the orientation of the magnetic flux field exerted by the strap 120 can be detected by the magnetic flux field sensor 138 and can be communicated to the processor/logic unit 140. The processor/logic unit 140 can then interpret the activity units as being generated by the user who is performing aerobic exercise. When the user orients the activity module 14 in the receptacle 122 so that the arrow-shaped pointer 106 points to the indicia W, the processor/logic unit 140 can interpret the output of the magnetic flux detector 138 as indicating the user activity units are being generated by the user who is performing some form of anaerobic exercise, e.g., weight lifting. When so oriented, the processor/logic unit 86 of the activity module 14 can add a multiplier to the calculations of the activity count. (The multiplier number may be changed via an input to the algorithm through the Bluetooth™ interface). The multiplier can alter the activity counts that can be transmitted to the application 12, so that each individual deflection (or back and forth deflection) may be transmitted to the application 12 as a singe count, e.g., in a normal anaerobic training mode, or "standard activity" mode or, for example, multiplied by 2 for intense anaerobic training, or multiplied by 3 for aerobic training, or by 4 for intense aerobic training. It will be understood that other multipliers and/or means of accounting for a single step or single exercise repetition, or the like, may be possible When the user is about to begin high intensity or "turbo" exercise activities, he/she can briefly depress the buttons 104. This can, e.g., place the activity module 14 temporarily in a high intensity or turbo physical exercise monitoring mode in which the activity units that are generated by the activity module 14 can be multiplied by an additional factor so that each deflection has a greater impact on the activity circle 116 than when in ("normal") weight training or aerobic training without the turbo function engaged. An indicator light 119 may be illuminated when the activity module 14 can be placed in the turbo exercise monitoring mode. At the end of the turbo exercise activities the user can again briefly depress the buttons 104 to exit the high intensity exercise mode, or alternately, the activity module 14 can automatically turn off the high intensity exercise monitoring mode when it senses a sustained decrease in the frequency of activity units.

As described above, the activity module 14 can be adapted to measure and record activity units in the following five physical activity modes: i) aerobic, ii) intense or turbo aerobic, iii) weight or muscle training, iv) intense or turbo weight training, and v) standard activity mode. The processor/logic unit 140 can, e.g., interpret one click of the accelerometer in each of the five physical activity modes as follows: i) in the aerobic exercise mode, one click can be equal to (A×1 repetition) activity unit, where A can be a predetermined constant coefficient, ii) in the turbo aerobic mode, one click can be equal to (A+×1 repetition) activity unit, where A+ can be a predetermined coefficient, iii) in the weight training mode, one click can be equal to (W×1 repetition) activity unit, where W can be a predetermined coefficient, iv) in the turbo weight training mode, one click can be equal to (W+×1 repetition) activity unit, where W+ can be a predetermined coefficient, and v) in the standard activity mode, one click can be equal to (R×1 repetition or alternatively time period) activity unit, where R can be a predetermined constant coefficient. These values can be altered, e.g., via the Bluetooth™ algorithm by the user, athletic coach or health professional to create unique exercise programs beyond those provide in the system 10.

It should be appreciated that the disclosed subject matter provides numerous advantages. For instance, in the event that the application 12 is implemented on a digital device D such as a smart phone, the system 10 can be therefore normally close at hand to the user throughout the day. This can encourage the user to accurately input food consumption close to the time it occurs. The method of utilizing food icons for inputting the type and portion size for food consumption, without the need for looking up and computing calories, can further encourage the user to more accurately and conveniently input food consumption and to do so close to the time it is or will be consumed. Likewise, wearing the activity module 14 can further contribute to the user conveniently and autonomously inputting the activity units in the systems 10. The system 10 features concise, powerful and completing graphical indicators on the health and fitness of the user, such as i) the fitness arc 34 which can provide, e.g., an energy balance that can be an indicator of the effectiveness of the user's daily weight and fitness management, ii) the health quotient 42 which can provide, e.g., an indicator of the health of the user for a particular extended time period, iii) the fluid an salt circles 31A and 31B, iv) the activity circle 38, the v) the Vit circle 82, and the like and vi) favorite food indicator(s) 56. Further, the system 10 can compensate(s) for user inaccuracies in food portion size estimates by assessing the user's energy balance including his/her intrinsic metabolism and adjusting the food estimates accordingly or simply automatically increasing or decreasing the food intake units, e.g., daily. The system also has the flexibly of operating on a combined mode, or an estimated mode in which the user does not utilize the activity module 14, and instead estimates his/her activity units.

For example, the estimated algorithm mode of the application 12 can begin with an assigned and fixed number of activity units. The assigned amount can be derived from the learning algorithm that runs when the activity module 14 is actually used to record all activity, or in cases where the activity module 14 has not been used, a value can be assigned based upon the users selected profile.

Figure 17:
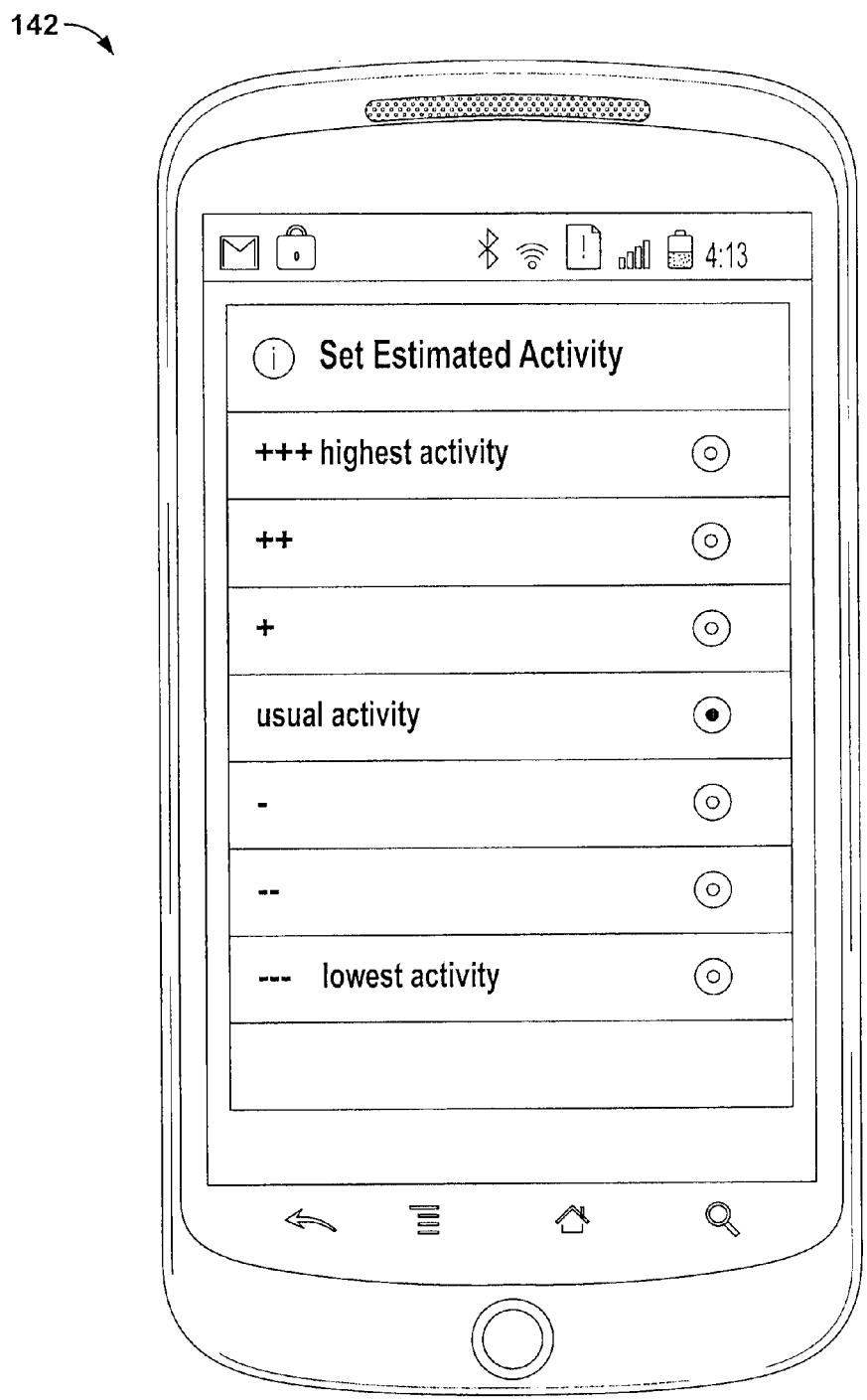
FIG. 17 is a user activity estimation input screen.

Referring to FIG. 17, the user can make a selection from an estimated activity page 142 that describes his/her activity. The entry of the estimated amount of activity can be input as often as the user chooses. If no entries are made, the algorithm can assume that the activity for that day was a usual or forecasted/assigned amount, or the like. Each user estimated activity update can apply to the time period from the last entry/estimation. Thus if 100 activity units were expected at 8 AM and the user selects "usual," then 100 units can be added to activity circle 116. Selection of a plus or minus option can alter the activity units forecasted/assigned for that period of time by plus or minus 10%, 20% or 30%. Fro example, the activity units entered might be 100, 120 or 80 etc.

The next time the user enters the estimated activity, the application 12 can have expected a certain number of activity units to have been performed since the last entry. Expected activity units can be the number registered to the activity circle if the user selects the "usual" option from the estimated activity page 142. The number of expected units can be determined by the amount of time that has past, since the user last registered activity by a selection from the estimated activity page 142. For example the algorithm might have expected the user to have registered 1000 activity units since the time of last entry, and if "+++" is selected, the algorithm can place 1300 units into the activity circle 116. If at the time of the next entry 2000 units would have been expected (i.e., 2000 units would have occurred in the time frame since the last entry) and "−−" had been selected, the algorithm can enter 1600 units into the activity circle 116.

If the estimated activity units are used to describe the majority of daily activity, but the user wishes to use the activity module 14 to quantify exercise, then the application 12 can process those activity units as a percentage of those expected during the time frame during which activity module 14 was in use and apply a 10%, 20%, or 30% increment to the activity count total. For example, if in the time frame between the last entry in the application 12 estimation-algorithm's algorithm the algorithm would expect 1000 units, but the user, instead of making a selection from the estimated activity page chooses to utilize the activity module 14 for entry of actual activity units, the algorithm can perform as follows:

for any number of activity units that the activity module 14 provides which are less than expected plus 20% (1200 activity units in the current example) the application can place the expected plus 10% units into the activity circle 116, (1100 activity units in the current example);

between an expected plus 20% and expected plus 30% the application 12 can add expected plus 20% to activity circle 116, (1200 units in the current example); and for any number of activity units above 30% of expected, then the expected plus 30% can be added to activity circle 116, (1300 units in the current example). The maximum allowed activity count can be an expected plus 30%, regardless of the actual number of activity counts (e.g., 1400 activity units would be entered as 1300 units to activity circle 116).

It should be noted that the disclosed subject matter can have numerous modifications and variations. For instance, users sponsored by a business or organization may receive downloads to the system 10. The business or organization may generate a rewards algorithm for the sponsored users by providing benefits such as financial rewards, music, cell phone minutes, video game access, etc.

In some embodiments, the device D may receive signals not only from an activity module 14, but also from other devices. For example, a body weight scale may be adapted to wirelessly transmit weight values to the digital device D, thereby automatically recording the user's actual weight in the system 10. Similarly, when test results items such as blood pressure are recorded, such information may be automatically transmitted to the digital device D. In other embodiments, the digital device D may interface with an electronic patient chart, allowing the user to upload information from the user medical chart directly to the system 10. In an embodiment, the system 10 may provide real time advice with respect to the user's choice of foods and activity to improve the prospect of reaching specific health and fitness goals, and the system 10 may consider factors such as whether the user is a long distance runner, whether the user is pregnant, elderly, and/or whether the user has health related diseases such as hypertension, diabetes, obesity, or anorexia. Having disclosed the apparatus and functions of the system 10, examples of some of the system 10 operational facilities are provided below.

Figure 18:
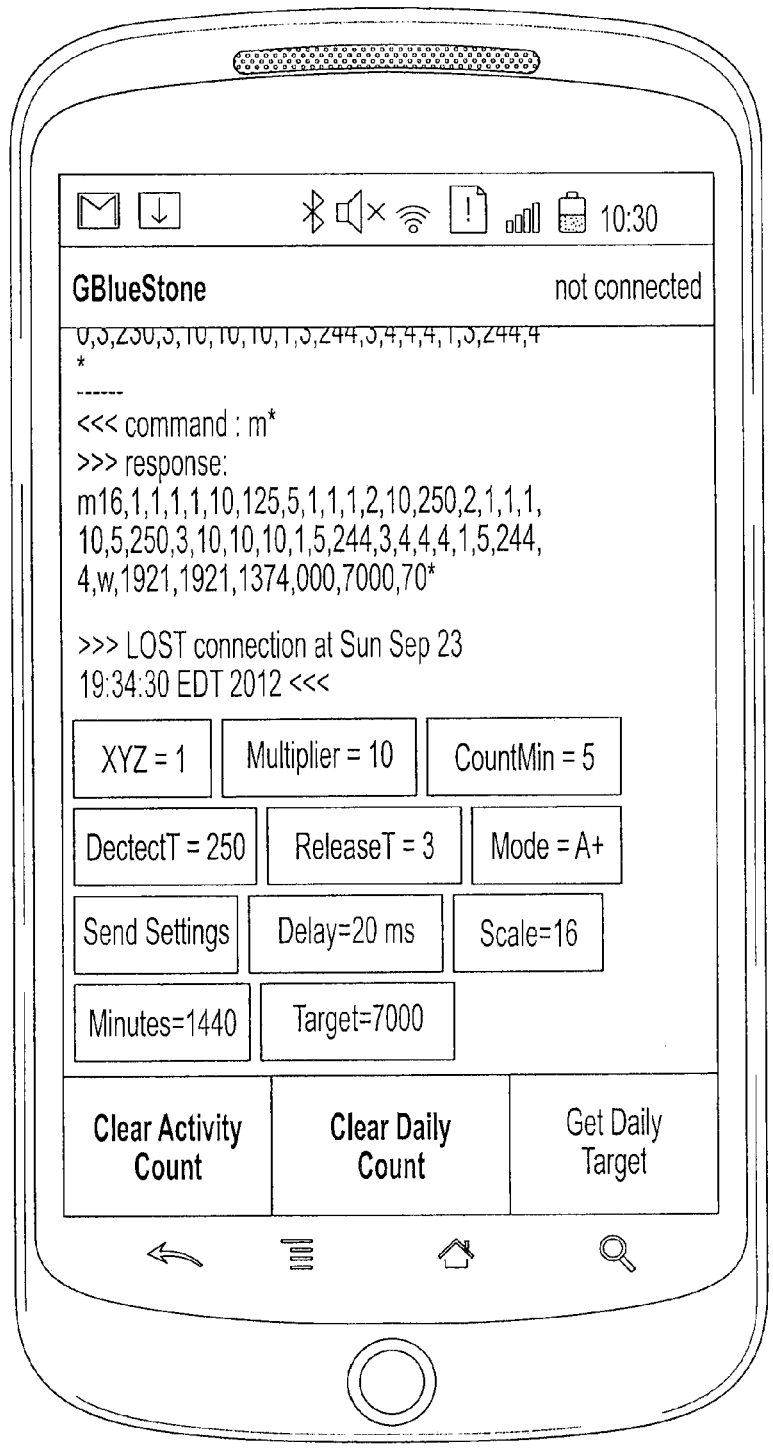
FIG. 18 is a screen showing a command string for controlling the performance of the activity module.
Figure 19A:
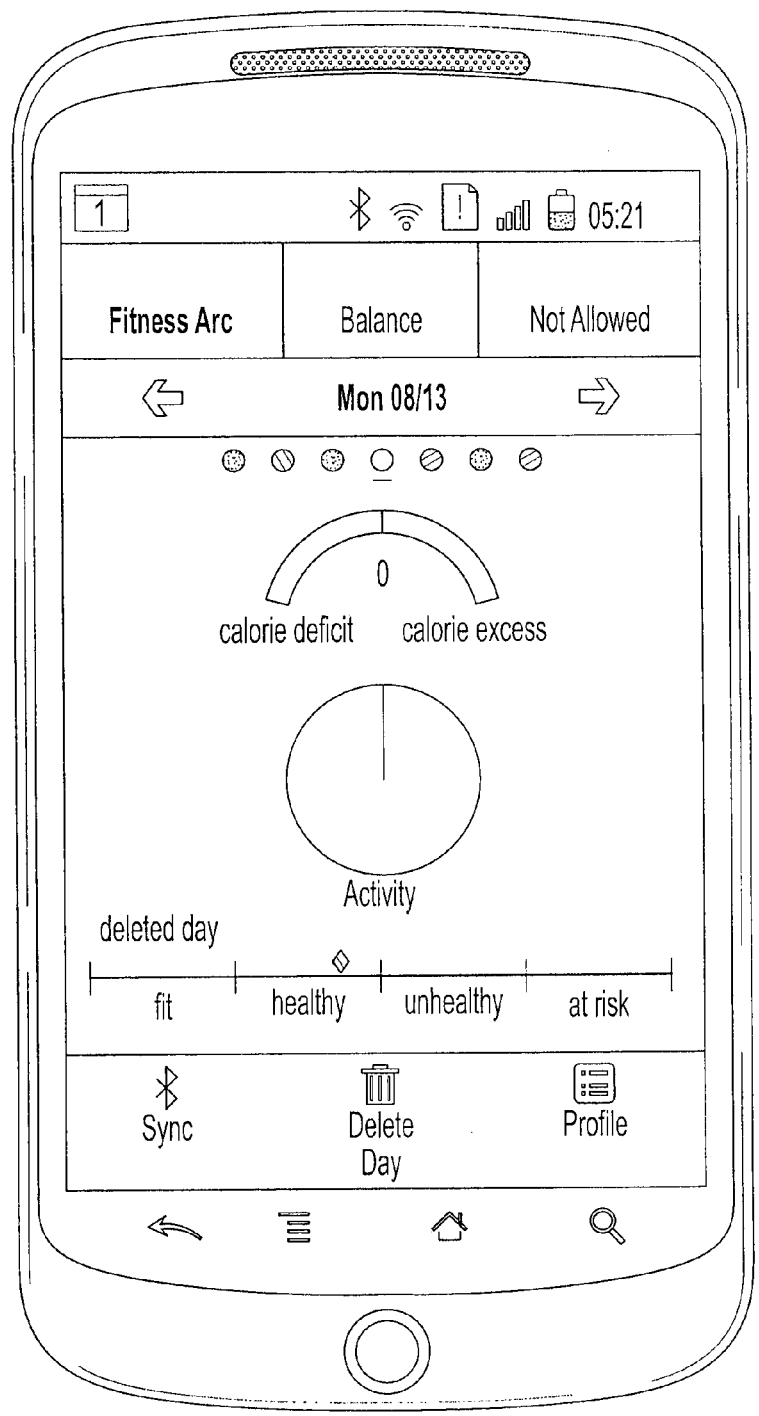
FIG. 19A is a screen showing a "deleted day" message.
Figure 19B:
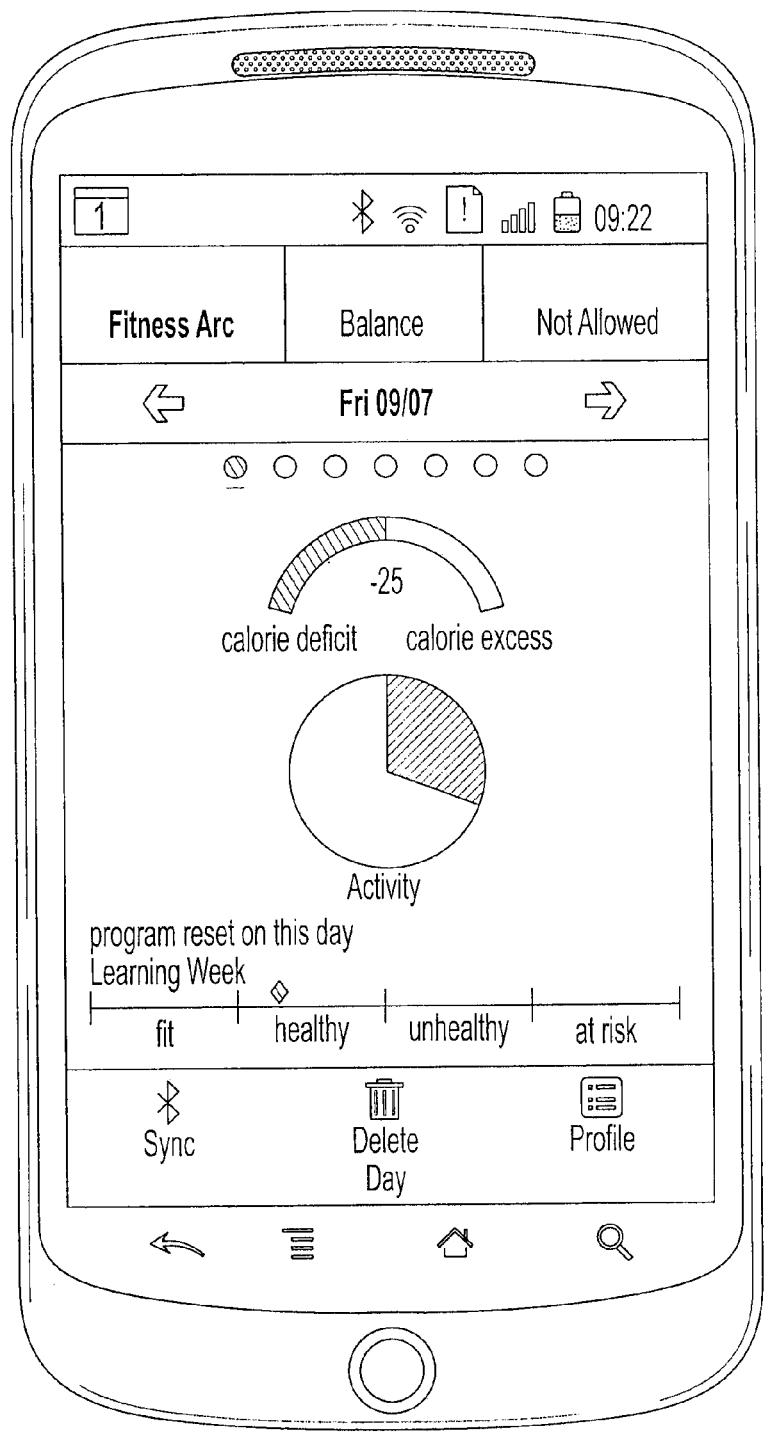
FIG. 19B is a screen showing a "algorithm reset on this day" message.

Referring to FIG. 18, the user may reprogram the activity module 14 (e.g., the five activity monitoring modes described hereinabove), e.g., via the application 10 and the Bluetooth™ transceiver of the digital device D. Also FIGS. 19A and 19B illustrate a facility to remove a day's input, which may be required should the user believe that data for a particular day are not correct or was not entered accurately.

The following is a disclosure by way of example of a computing device which may be used with the presently disclosed subject matter. The description of the various components of a computing device is not intended to represent any particular architecture or manner of interconnecting the components. Other systems that have fewer or more components may also be used with the disclosed subject matter. A communication device may constitute a form of a computing device and may at least emulate a computing device. The computing device may include an inter-connect (e.g., bus and system core logic), which can interconnect such components of a computing device to a data processing device, such as a processor(s) or microprocessor(s), or other form of partly or completely programmable or pre-programmed device, e.g., hard wired and/or application specific integrated circuit ("ASIC") customized logic circuitry, such as a controller or microcontroller, a digital signal processor, or any other form of device that can fetch instructions, operate on pre-loaded/pre-programmed instructions, and/or follow instructions found in hard-wired or customized circuitry, to carry out logic operations that, together, perform steps of and whole processes and functionalities as described in the present disclosure.

In this description, various functions, functionalities and/or operations may be described as being performed by or caused by software program code to simplify description. However, those skilled in the art will recognize what is meant by such expressions is that the functions resulting from execution of the program code/instructions are performed by a computing device as described above, e.g., including a processor, such as a microprocessor, microcontroller, logic circuit or the like. Alternatively, or in combination, the functions and operations can be implemented using special purpose circuitry, with or without software instructions, such as using Application-Specific Integrated Circuit (ASIC) or Field-Programmable Gate Array (FPGA), which may be programmable, partly programmable or hard wired. The application specific integrated circuit ("ASIC") logic may be such as gate arrays or standard cells, or the like, implementing customized logic by metalization(s) interconnects of the base gate array ASIC architecture or selecting and providing metalization(s) interconnects between standard cell functional blocks included in a manufacturers library of functional blocks, etc. Embodiments can thus be implemented using hardwired circuitry without program software code/instructions, or in combination with circuitry using programmed software code/instructions.

Thus, the techniques are limited neither to any specific combination of hardware circuitry and software, nor to any particular tangible source for the instructions executed by the data processor(s) within the computing device. While some embodiments can be implemented in fully functioning computers and computer systems, various embodiments are capable of being distributed as a computing device including, e.g., a variety of forms and capable of being applied regardless of the particular type of machine or tangible computer-readable media used to actually effect the performance of the functions and operations and/or the distribution of the performance of the functions, functionalities and/or operations.

The interconnect may connect the data processing device to define logic circuitry including memory. The interconnect may be internal to the data processing device, such as coupling a microprocessor to on-board cache memory, or external (to the microprocessor) memory such as main memory, or a disk drive, or external to the computing device, such as a remote memory, a disc farm or other mass storage device(s), etc. Commercially available microprocessors, one or more of which could be a computing device or part of a computing device, include a PA-RISC series microprocessor from Hewlett-Packard Company, an 80×86 or Pentium series microprocessor from Intel Corporation, a PowerPC microprocessor from IBM, a Sparc microprocessor from Sun Microsystems, Inc, or a 68xxx series microprocessor from Motorola Corporation as examples.

The inter-connect in addition to interconnecting such as microprocessor(s) and memory may also interconnect such elements to a display controller and display device, and/or to other peripheral devices such as input/output (I/O) devices, e.g., through an input/output controller(s). Typical I/O devices can include a mouse, a keyboard(s), a modem(s), a network interface(s), printers, scanners, video cameras and other devices which are well known in the art. The interconnect may include one or more buses connected to one another through various bridges, controllers and/or adapters. In one embodiment the I/O controller may include a USB (Universal Serial Bus) adapter for controlling USB peripherals, and/or an IEEE-1394 bus adapter for controlling IEEE-1394 peripherals.

The memory may include any tangible computer-readable media, which may include but are not limited to recordable and non-recordable type media such as volatile and non-volatile memory devices, such as volatile RAM (Random Access Memory), typically implemented as dynamic RAM (DRAM) which requires power continually in order to refresh or maintain the data in the memory, and non-volatile ROM (Read Only Memory), and other types of non-volatile memory, such as a hard drive, flash memory, detachable memory stick, etc. Non-volatile memory typically may include a magnetic hard drive, a magnetic optical drive, or an optical drive (e.g., a DVD ROM, a CD ROM, a DVD or a CD), or other type of memory system which maintains data even after power is removed from the system.

A server could be made up of one or more computing devices. Servers can be utilized, e.g., in a network to host a network database, compute necessary variables and information from information in the database(s), store and recover information from the database(s), track information and variables, provide interfaces for uploading and downloading information and variables, and/or sort or otherwise manipulate information and data from the database(s). In one embodiment a server can be used in conjunction with other computing devices positioned locally or remotely to perform certain calculations and other functions as may be mentioned in the present application.

At least some aspects of the disclosed subject matter can be embodied, at least in part, utilizing programmed software code/instructions. That is, the functions, functionalities and/or operations techniques may be carried out in a computing device or other data processing system in response to its processor, such as a microprocessor, executing sequences of instructions contained in a memory, such as ROM, volatile RAM, non-volatile memory, cache or a remote storage device. In general, the routines executed to implement the embodiments of the disclosed subject matter may be implemented as part of an operating system or a specific application, component, program, object, module or sequence of instructions usually referred to as "computer programs," or "software." The computer programs typically comprise instructions stored at various times in various tangible memory and storage devices in a computing device, such as in cache memory, main memory, internal or external disk drives, and other remote storage devices, such as a disc farm, and when read and executed by a processor(s) in the computing device, cause the computing device to perform a method(s), e.g., process and operation steps to execute an element(s) as part of some aspect(s) of the method(s) of the disclosed subject matter.

A tangible machine readable medium can be used to store software and data that, when executed by a computing device, causes the computing device to perform a method(s) as may be recited in one or more accompanying claims defining the disclosed subject matter. The tangible machine readable medium may include storage of the executable software program code/instructions and data in various tangible locations, including for example ROM, volatile RAM, non-volatile memory and/or cache. Portions of this program software code/instructions and/or data may be stored in any one of these storage devices. Further, the program software code/instructions can be obtained from remote storage, including, e.g., through centralized servers or peer to peer networks and the like. Different portions of the software program code/instructions and data can be obtained at different times and in different communication sessions or in a same communication session.

The software program code/instructions and data can be obtained in their entirety prior to the execution of a respective software application by the computing device. Alternatively, portions of the software program code/instructions and data can be obtained dynamically, e.g., just in time, when needed for execution. Alternatively, some combination of these ways of obtaining the software program code/instructions and data may occur, e.g., for different applications, components, programs, objects, modules, routines or other sequences of instructions or organization of sequences of instructions, by way of example. Thus, it is not required that the data and instructions be on a single machine readable medium in entirety at any particular instant of time.

In general, a tangible machine readable medium includes any tangible mechanism that provides (i.e., stores) information in a form accessible by a machine (i.e., a computing device), which may be included, e.g., in a communication device, a network device, a personal digital assistant, a mobile communication device, whether or not able to download and run applications from the communication network, such as the Internet, e.g., an I-Phone®, Blackberry®, Droid™ or the like, a manufacturing tool, or any other device including a computing device, comprising one or more data processors, etc.

In one embodiment, a user terminal can be a computing device, such as in the form of or included within a PDA, a cellular phone, a notebook computer, a personal desktop computer, etc. Alternatively, the traditional communication client(s) may be used in some embodiments of the disclosed subject matter.

While some embodiments of the disclosed subject matter have been described in the context of fully functioning computing devices and computing systems, those skilled in the art will appreciate that various embodiments of the disclosed subject matter are capable of being distributed, e.g., as a program product in a variety of forms and are capable of being applied regardless of the particular type of computing device machine or computer-readable media used to actually effect the distribution.

The disclosed subject matter may be described with reference to block diagrams and operational illustrations of methods and devices to provide a system and methods according to the disclosed subject matter. It will be understood that each block of a block diagram or other operational illustration (herein collectively, "block diagram"), and combination of blocks in a block diagram, can be implemented by means of analog or digital hardware and computer program instructions. These computing device software program code/instructions can be provided to the computing device such that the instructions, when executed by the computing device, e.g., on a processor within the computing device or other data processing apparatus, the program software code/instructions cause the computing device to perform functions, functionalities and operations of a method(s) according to the disclosed subject matter, as recited in the accompanying claims, with such functions, functionalities and operations specified in the block diagram.

It will be understood that in some possible alternate implementations, the function, functionalities and operations noted in the blocks of a block diagram may occur out of the order noted in the block diagram. For example, the function noted in two blocks shown in succession can in fact be executed substantially concurrently or the functions noted in blocks can sometimes be executed in the reverse order, depending upon the function, functionalities and operations involved. Therefore, the embodiments of methods presented and described as a flowchart(s) in the form of a block diagram in the present application are provided by way of example in order to provide a more complete understanding of the disclosed subject matter. The disclosed flow and concomitantly the method(s) performed as recited in the accompanying claims are not limited to the functions, functionalities and operations illustrated in the block diagram and/or logical flow presented herein. Alternative embodiments are contemplated in which the order of the various functions, functionalities and operations may be altered and in which sub-operations described as being part of a larger operation may be performed independently or performed differently than illustrated or not performed at all.

Although some of the drawings may illustrate a number of operations in a particular order, functions, functionalities and/or operations which are not now known to be order dependent, or become understood to not be order dependent, may be reordered and other operations may be combined or broken out. While some reordering or other groupings may have been specifically mentioned in the present application, others will be or may become apparent to those of ordinary skill in the art and so the disclosed subject matter does not present an exhaustive list of alternatives. It should also be recognized that the aspects of the disclosed subject matter may be implemented in parallel or seriatim in hardware, firmware, software or any combination(s) thereof co-located or remotely located, at least in part, from each other, e.g., in arrays or networks of computing devices, over interconnected networks, including the Internet, and the like.

It will be understood that the present patent application discloses The disclosed subject matter is described in the present application with reference to one or more specific exemplary embodiments thereof. Such embodiments are provided by way of example only. It will be evident that various modifications may be made to the disclosed subject matter without departing from the broader spirit and scope of the disclosed subject matter as set forth in the appended claims. The specification and drawings are, accordingly, to be regarded in an illustrative sense for explanation of aspects of the disclosed subject matter rather than a restrictive or limiting sense. Numerous variations, changes, and substitutions will now occur to those skilled in the art without departing from the disclosed subject matter. It should be understood that various alternatives to the embodiments of the disclosed subject matter described herein may be employed in practicing the disclosed subject matter. It is intended that the following claims define the scope of the disclosed subject matter and that methods and structures within the scope of these claims and their equivalents be covered thereby.

It will be understood that the disclosed subject matter may comprise a fitness management method and apparatus which may comprise collecting food intake information for actual or expected food intake of a user over a first period of time and converting the food intake information into food intake units for the first period of time; collecting activity information for actual or expected activity by the user over the first period of time and converting the food intake information into food intake units for the user for the first period of time; collecting weight information representing a change in weight of the user over the first period of time; calculating, via a computing device, a calculated intrinsic metabolic rate for the user for the first period of time; collecting food intake information for actual or expected food intake of a user over a second period of time and converting the food intake information into food intake units for the second period of time; collecting activity information for actual or expected activity of a user over the second period of time and converting the activity information into activity units for the second period of time; calculating, via the computing device, a predicted change in weight for the second period of time based upon the calculated intrinsic metabolic rate for the user over the first period of time; collecting weight information representing an actual change in weight of the user over the second period of time; comparing the predicted change in weight for the second period of time to the actual change in weight for the second period of time; determining, via the computing device, an updated calculated intrinsic metabolic rate for the user based at least in part upon the difference between the predicted change in weight for the second period of time and the actual change in weight for the second period of time. The method and apparatus may further comprise collecting food intake information for actual or expected food intake of a user over a third period of time and converting the food intake information into food intake units for the third period of time; collecting activity information for actual or expected activity of a user over the third period of time and converting the activity information into activity units for the third period of time; calculating, via the computing device, a predicted change in weight for the third period of time based upon the updated calculated intrinsic metabolic rate for the user over the first period of time; collecting weight information representing an actual change in weight of the user over the second period of time; further updating, via the computing device, the updated calculated intrinsic metabolic rate for the user based at least in part upon the difference between the predicted change in weight for the third period of time and the actual change in weight for the third period of time. The method and apparatus may further comprise: displaying, via the computing device, at least one of an accumulation of food intake units and an accumulation of activity units over at least one of the first period of time, the second period of time and the third period of time. The apparatus and method may further comprise dividing the first period of time into a selected number of first sub-time periods; collecting food intake information for actual or expected food intake of the user over each of the first sub-time periods during the first period of time and converting the food intake information into food intake units for each of the first sub-time units during the first period of time; collecting activity information for actual or expected activity by the user over each of the first sub-time periods and converting the activity information into activity units for the user for each of the sub-time periods during the first period of time; collecting weight information representing a change in weight of the user over at least a last of the first sub-time periods and a first of the first sub-time periods to determine a change in weight of the user over the first period of time; dividing the second period of time into a selected number of second sub-time periods; collecting food intake information for actual or expected food intake of the user over each of the second sub-time periods during the second period of time and converting the food intake information into food intake units for each of the second sub-time units during the second period of time; collecting activity information for actual or expected activity by the user over each of the second sub-time periods and converting the activity information into activity units for the user for each of the second sub-time periods during the second period of time; collecting weight information representing a change in weight of the user over at least a last of the second sub-time periods to determine a change in weight of the user over the second period of time. The method and apparatus may further comprise dividing the third period of time into a selected number of third sub-time periods; collecting food intake information for actual or expected food intake of the user over each of the third sub-time periods during the third period of time and converting the food intake information into food intake units for each of the third sub-time periods during the third period of time; collecting activity information for actual or expected activity by the user over each of the third sub-time periods and converting the activity information into activity units for the user for each of the third sub-time periods during the third period of time; and collecting weight information representing a change in weight of the user over at least a last of the third sub-time periods to determine a change in weight of the user over the third period of time. The method and apparatus may further comprise determining an updated calculated intrinsic metabolic rate for the user based at least in part upon the difference between the predicted change in weight for the second period of time and the actual change in weight for the second period of time and determining a further updated calculated intrinsic metabolic rate for the user based at least in part upon the difference between the predicted change in weight for the second period of time and the actual change in weight for the second period of time. A machine readable medium storing instructions that, when executed by a computing device cause the computing device to perform a fitness management method is disclosed in which the method may comprising collecting food intake information for actual or expected food intake of a user over a first period of time and converting the food intake information into food intake units for the first period of time; collecting activity information for actual or expected activity by the user over the first period of time and converting the food intake information into food intake units for the user for the first period of time; collecting weight information representing a change in weight of the user over the first period of time; calculating a calculated intrinsic metabolic rate for the user for the first period of time; collecting food intake information for actual or expected food intake of a user over a second period of time and converting the food intake information into food intake units for the second period of time; collecting activity information for actual or expected activity of a user over the second period of time and converting the activity information into activity units for the second period of time; calculating a predicted change in weight for the second period of time based upon the calculated intrinsic metabolic rate for the user over the first period of time; collecting weight information representing an actual change in weight of the user over the second period of time; comparing the predicted change in weight for the second period of time to the actual change in weight for the second period of time; determining an updated calculated intrinsic metabolic rate for the user based at least in part upon the difference between the predicted change in weight for the second period of time and the actual change in weight for the second period of time.

The system and method may comprise a food intake information and weight information input unit; an activity information collection and input unit separate from the food intake information and weight information input unit and adapted to move with a portion a body of the user. At least one of the food intake information and weight information input unit and the activity information collection and input may comprise the computing device. The system and method may comprise the food information and weight information input unit comprising a portable user device having a touch screen display. The system and method may comprise the activity information input unit comprising an accelerometer for detecting activity repetitions. At least one of the food intake information and weight information input unit and the activity input unit the computing device may be configured to assign weighted values to each activity repetition according to one of the type and intensity of the activity and at least one of the repetitions detected. The system and method may comprise the food intake information input and weight information input unit further comprising the computing device configured to display a prediction of fitness performance based at least in part on a current metabolic rate for the user. The current metabolic rate may be computed by the computing device based on a difference between a predicted change in weight for a selected period of time and an actual measured change in weight for the selected period of time. The displayed prediction may comprise a graphical fitness prediction chart including perhaps a graphical fitness prediction chart.

It will also be understood that the embodiments described herein are merely exemplary and that a person skilled in the art may make many variations and modifications without departing from the spirit and scope of the invention. For instance, all such variations and modifications can be intended to be included within the scope of the invention as defined in the appended claims.

What is claimed is:

1. A non-transitory machine readable medium storing instructions that, when executed by a computing device, cause the computing device to perform a method for instantaneously and continuously assessing real time energy balance for fitness management, comprising:

(a) collecting food intake information for actual or expected food intake of a user over a specified period of time and contemporaneously converting the food intake information into food intake energy units for the specified period of time, wherein the food intake energy units are based on energy content of one food compared to another without relying on user-inputted caloric values;

(b) collecting by a device activity information for actual or expected activity by the user over the specified period of time and contemporaneously converting the activity information into activity energy units for the user for the specified period of time;

(c) instantaneously deriving, via a computing device, a calculated currently determined constant that reflects efficiency, which is a rate at which the user extracts energy from the food units that can be referenced against predicted and actual changes in weight, wherein the constant is a surrogate for intrinsic metabolic rate;

(d) instantaneously calculating by an algorithm from the calculated currently determined constant in (c) a predicted energy balance for the user, by:
  (i) calculating a ratio of an amount of activity units expected divided by an amount of activity observed;
  (ii) calculating a ratio of an amount of food units expected divided by an amount of food units observed;
  (iii) weighting the ratio in (a) against the ratio in (b) according to goals of the user; and
  (iv) modifying the weighted ratio in (iii) by a rate at which the user performs the actual or expected activity;

(e) instantaneously predicting a change in weight from the predicted energy balance;

(f) determining and reporting a fitness level of the user in real time comprising a fitness arc and a health quotient, based on the efficiency of energy consumption so that user can modify or continue user's fitness behavior.

2. The non-transitory machine readable medium of claim 1, wherein collecting food intake information in (a) comprises inputting type and portion of food visually.

3. The non-transitory machine readable medium of claim 1, further comprising displaying the predicted energy balance graphically.

4. The non-transitory machine readable medium of claim 1, wherein in (d) the algorithm maintains an accurate prediction of weight change in (e) by adjusting to inaccuracies in food intake information, activity information or both.

5. The non-transitory machine readable medium of claim 1, wherein the calculated currently determined constant that reflects efficiency is recalculated, new values are assigned, or both, when the algorithm cannot make predictions of energy balance and change in weight accurately.

6. The non-transitory machine readable medium of claim 1, wherein the value of the food intake energy units and activity energy units are referenced against actual indicated weight change and the calculated currently determined constant that reflects efficiency and that serves as a surrogate for intrinsic metabolic rate of the user.

7. The non-transitory machine readable medium of claim 1, wherein the predicted energy balance comprises a relationship between:
  a. a first power equation in which power P is the rate at which energy can be transferred or consumed and that measures a rate of energy transfer; and
  b. a second power equation in which power P' is the rate at which work can be performed, and that measures movement of a fixed mass over a specified distance per unit time.

8. The non-transitory machine readable medium of claim 7, wherein the rate of energy transfer is estimated from a rate at which weight is gained or lost.

9. The non-transitory machine readable medium of claim 7, wherein the amount of food units expected is the number of food energy units that, for a specified time of day and for actual/predicted activity levels the user can consume.

10. The non-transitory machine readable medium of claim 7, wherein the first and second power equations are given a relative weight and summed to produce a percentage change in observed versus predicted food energy units consumed and activity energy unit expended.

11. The non-transitory machine readable medium of claim 7, wherein the activity energy unit expected is based upon history of amount and type of activity performed by the user.

12. The non-transitory machine readable medium of claim 1, the method further comprising adjusting food allowance for the user throughout the specified time based on what activity is expected and what activity has actually occurred.

13. The non-transitory machine readable medium of claim 1, wherein the predicted energy balance between food intake energy units, activity energy units and the calculated currently determined constant that reflects efficiency and that serves as a surrogate for intrinsic metabolic rate is periodically updated.

14. The non-transitory machine readable medium of claim 1, wherein the calculated currently determined constant that reflects efficiency and that serves as a surrogate for intrinsic metabolic rate corrects variance between predicted energy consumption and observed energy consumption.

15. The non-transitory machine readable medium of claim 1, wherein value of a food energy unit or an activity energy unit is defined by how the user inputs data.

16. The non-transitory machine readable medium of claim 1, wherein the algorithm creates an ongoing user profile of intrinsic metabolism, activity, food choice and food amount that is unique to the user.

17. The non-transitory machine readable medium of claim 1, wherein the food intake information is a graphic input.

18. The non-transitory machine readable medium of claim 17, wherein the graphic input is an iconic food item.

19. The non-transitory machine readable medium of claim 1, wherein the collecting activity information for actual activity is achieved by wireless transmission by a motion sensor.

20. The non-transitory machine readable medium of claim 19, wherein the motion sensor is an accelerometer.

21. The non-transitory machine readable medium of claim 1, wherein the computing device is selected from the group consisting of a smart cell phone, a tablet device, a PDA, and a personal computer.

22. The non-transitory machine readable medium of claim 1, wherein the food intake information for actual or expected food intake of the user over a specified period of time is a first period of time, wherein the first period of time includes at least a part or parts of a first week, and
    wherein a further specified period of time is a second period of time,
    wherein the second period of time includes at least a part or parts of a second subsequent week.

23. A system for instantaneously and continuously assessing real time energy balance for fitness management comprising:
    a computing device configured to:
    (a) collect food intake information for actual or expected food intake of a user over a specified period of time and contemporaneously converting the food intake information into food intake units for the specified period of time, wherein the food intake energy units are based on energy content of one food compared to another without relying on user-inputted caloric values;
    (b) collect by a device activity information for actual or expected activity by the user over the specified period of time and contemporaneously converting the activity information into activity units for the user for the first period of time;
    (c) instantaneously derive, via a computing device, a calculated currently determined constant that reflects efficiency, which is a rate at which the user extracts energy from the food units that can be referenced against predicted and actual changes in weight, wherein the constant is a surrogate for intrinsic metabolic rate;
    (d) instantaneously calculate by an algorithm from the calculated currently determined constant in (c) a predicted energy balance for the user, by:
        (i) calculating a ratio of an amount of activity units expected divided by an amount of activity observed;
        (ii) calculating a ratio of an amount of food units expected divided by an amount of food units observed;
        (iii) weighting the ratio in (a) against the ratio in (b) according to goals of the user; and
        (iv) modifying the weighted ratio in (iii) by a rate at which the user performs the actual or expected activity;
    (e) instantaneously predict a change in weight from the predicted energy balance;
    (f) determine and report a fitness level of the user in real time comprising a fitness arc and a health quotient, based on the efficiency of energy consumption so that user can modify or continue user's fitness behavior.

24. The fitness management system of claim 23, wherein collecting food intact information in (a) comprises inputting type and portion of food visually.

25. The fitness management system of claim 23, further comprising displaying the predicted energy balance graphically.

26. The fitness management system of claim 23, wherein in (d) the algorithm maintains an accurate prediction of weight change in (e) by adjusting to inaccuracies in food intake information, activity information or both.

27. The fitness management system of claim 23, wherein the calculated currently determined constant that reflects efficiency is recalculated, new values are assigned, or both, when the algorithm cannot make predictions of energy balance and change in weight accurately.

28. The fitness management system of claim 23, wherein value of the food intake energy units and activity energy units are referenced against actual indicated weight change and the calculated currently determined constant that reflects efficiency and that serves as a surrogate for intrinsic metabolic rate of the user.

29. The fitness management system of claim 23, wherein the predicted energy balance comprises a relationship between:
    a. a first power equation in which power P is the rate at which energy can be transferred or consumed and that measures a rate of energy transfer; and
    b. a second power equation in which power P' is the rate at which work can be performed, and that measures movement of a fixed mass over a specified distance per unit time.

30. The fitness management system of claim 23, wherein the rate of energy transfer is estimated from a rate at which weight is gained or lost.

31. The fitness management system of claim 23, wherein the amount of food units expected is the number of food energy units that, for a specified time of day and for actual/predicted activity levels the user can consume.

32. The fitness management system of claim 23, wherein the first and second power equations are given a relative weight and summed to produce a percentage change in observed versus predicted food energy units consumed and activity energy unit expended.

33. The fitness management system of claim 23, wherein the activity energy unit expected is based upon history of amount and type of activity performed by the user.

34. The fitness management system of claim 23, further comprising adjusting food allowance for the user throughout the specified time based on what activity is expected and what activity has actually occurred.

35. The fitness management system of claim 23, wherein the predicted energy balance between food intake energy units, activity energy units and the calculated currently determined constant that reflects efficiency and that serves as a surrogate for intrinsic metabolic rate is periodically updated.

36. The fitness management system of claim 23, wherein the calculated currently determined constant that reflects efficiency and that serves as a surrogate for intrinsic metabolic rate corrects variance between predicted energy consumption and observed energy consumption.

37. The fitness management system of claim 23, wherein value of a food energy unit or an activity energy unit is defined by how the user inputs data.

38. The fitness management system of claim 23, wherein the algorithm creates an ongoing user profile of intrinsic metabolism, activity, food choice and food amount that is unique to the user.

39. The fitness management system of claim 23, wherein the food intake information is a graphic input.

40. The fitness management system of claim 39, wherein the graphic input is an iconic food item.

41. The fitness management system of claim 23, wherein the collecting activity information for actual activity is achieved by wireless transmission by a motion sensor.

42. The fitness management system of claim 41, wherein the motion sensor is an accelerometer.

43. The fitness management system of claim 23, wherein the computing device is selected from the group consisting of a smart cell phone, a tablet device, a PDA, and a personal computer.

* * * * *

UNITED STATES PATENT AND TRADEMARK OFFICE
CERTIFICATE OF CORRECTION

| | | |
|---|---|---|
| PATENT NO. | : 9,183,498 B2 | Page 1 of 1 |
| APPLICATION NO. | : 13/743718 | |
| DATED | : November 10, 2015 | |
| INVENTOR(S) | : David B. Landers | |

It is certified that error appears in the above-identified patent and that said Letters Patent is hereby corrected as shown below:

On the title page please add the following Item (63)

-- Related U.S. Application Data --

-- Continuation-in-part of application No. 13/036,151 filed on February 28, 2011. --

Signed and Sealed this
Twenty-third Day of February, 2016

Michelle K. Lee
*Director of the United States Patent and Trademark Office*